(12) United States Patent
Kawashima et al.

(10) Patent No.: US 9,402,647 B2
(45) Date of Patent: Aug. 2, 2016

(54) SURGICAL SYSTEM

(71) Applicant: OLYMPUS CORPORATION, Tokyo (JP)

(72) Inventors: Ko Kawashima, Musashino (JP); Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 97 days.

(21) Appl. No.: 14/520,912

(22) Filed: Oct. 22, 2014

(65) Prior Publication Data

US 2015/0127038 A1  May 7, 2015

Related U.S. Application Data

(63) Continuation of application No. PCT/JP2014/052726, filed on Feb. 6, 2014.

(60) Provisional application No. 61/764,187, filed on Feb. 13, 2013.

(51) Int. Cl.
*A61B 17/32* (2006.01)
*A61B 18/00* (2006.01)
*A61N 7/02* (2006.01)

(52) U.S. Cl.
CPC . *A61B 17/320068* (2013.01); *A61B 17/320092* (2013.01); *A61B 2018/00988* (2013.01); *A61N 7/02* (2013.01)

(58) Field of Classification Search
None
See application file for complete search history.

(56) References Cited

U.S. PATENT DOCUMENTS 5,413,550 A * 5/1995 Castel ............... A61H 23/0245
601/2
8,320,573 B2 * 11/2012 Lundh ................ H04R 25/70
381/60

(Continued)

FOREIGN PATENT DOCUMENTS

EP  2 283 780 A2  2/2011
JP  A-2000-185052  7/2000

(Continued)

OTHER PUBLICATIONS

International Search Report issued in PCT/JP2014/052726 mailed Apr. 22, 2014 (with translation).

*Primary Examiner* — Mohamed Barakat
(74) *Attorney, Agent, or Firm* — Oliff PLC

(57) ABSTRACT

A surgical system has an ultrasound treatment instrument having an ultrasound transducer, a power supply apparatus to which the ultrasound treatment instrument is detachably connected, an energy supply section that supplies drive energy to the ultrasound transducer, a clock that measures a present time, a time updating section that outputs the present time, a storage section that stores a final updated time that is updated finally in the present time, and a number of times of use, a time period calculation section that calculates a non-connection time period of the ultrasound treatment instrument to the power supply apparatus, and a processing section that performs processing of generating an update signal that causes the number of times of use to be updated in accordance with a determination result with respect to the non-connection time period and a result of determination with respect to a parameter.

17 Claims, 24 Drawing Sheets

(56) References Cited

U.S. PATENT DOCUMENTS

| | | | |
|---|---|---|---|
| 2005/0070800 A1 | 3/2005 | Takahashi | |
| 2008/0275348 A1* | 11/2008 | Catt | A61B 5/1112 600/483 |
| 2009/0018623 A1 | 1/2009 | Levinson et al. | |
| 2010/0145332 A1* | 6/2010 | Shibata | A61B 17/320068 606/41 |
| 2010/0280374 A1* | 11/2010 | Roberts | A61N 5/1001 600/439 |
| 2011/0034910 A1 | 2/2011 | Ross et al. | |
| 2012/0078278 A1 | 3/2012 | Bales, Jr. et al. | |
| 2013/0018400 A1* | 1/2013 | Milton | A61B 17/32002 606/167 |

FOREIGN PATENT DOCUMENTS

| | | |
|---|---|---|
| JP | A-2003-038423 | 2/2003 |
| JP | A-2003-052717 | 2/2003 |
| JP | A-2010-88707 | 4/2010 |
| JP | A-2010-533054 | 10/2010 |
| WO | WO 2009/011708 A1 | 1/2009 |

* cited by examiner

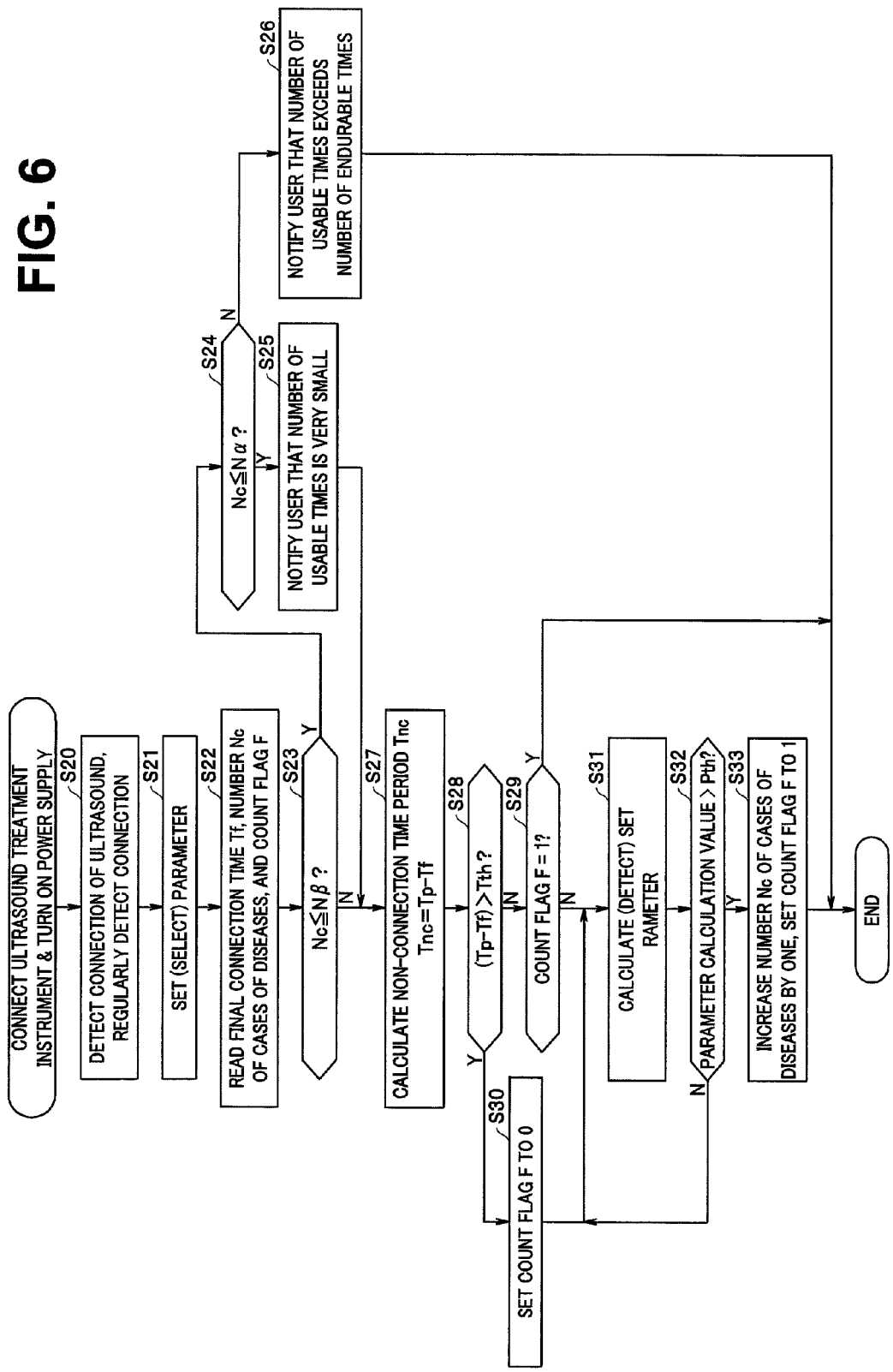

| NON-CONNECTION TIME PERIOD | CAPACITANCE THRESHOLD VALUE |
|---|---|
| 10 MINUTES TO 20 MINUTES | Cn+240(pF) |
| 20 MINUTES TO 30 MINUTES | Cn+220(pF) |
| 30 MINUTES TO 40 MINUTES | Cn+150(pF) |
| 40 MINUTES TO 50 MINUTES | Cn+100(pF) |
| 50 MINUTES TO 1 HOUR | Cn+80(pF) |

SURGICAL SYSTEM

CROSS REFERENCE TO RELATED APPLICATION

This application is a continuation application of PCT/JP2014/052726 filed on Feb. 6, 2014 and claims benefit of U.S. Provisional Patent Application No. 61/764,187 filed in the U.S.A. on Feb. 13, 2013, the entire contents of which are incorporated herein by this reference.

BACKGROUND OF THE INVENTION

1. Field of the Invention

The present invention relates to a surgical system including an ultrasound treatment instrument.

2. Description of the Related Art

In recent years, an ultrasound treatment instrument including an ultrasound transducer has been widely used as a surgical system that performs treatment such as dissection and excision by applying ultrasound vibration energy to living tissue of an object to be treated in a patient.

Further, an ultrasound treatment instrument that is used in treatment for one case of a disease is repeatedly used after sterilization or the like by an autoclave apparatus or the like is applied to the ultrasound treatment instrument and the ultrasound treatment instrument is set in a clean state. In the ultrasound treatment instrument which is used by repeating treatment by ultrasound vibration energy like this, degradation of the characteristics of the ultrasound transducer occurs by repetition of the treatment by the ultrasound vibration energy.

Therefore, for the ultrasound treatment instrument, the number of endurable times or the like as the number of usable times corresponding to a lifespan is set in advance.

In the systems including ultrasound treatment instruments as above, some systems include functions of determining whether or not the ultrasound treatment reaches the lifespan which is set in advance.

For example, Japanese Patent Application Laid-Open Publication No. 2010-88707 as the first conventional example discloses an apparatus including means that reads identification information provided in a probe that is used in energy treatment of ultrasound or the like, means that retains probe information which correlates the use history information including a sum of the number of times of output with a maximum output of the energy outputted from a generator and the number of times of output with a set output, and a sum of an output time period with the maximum output and an output time period with the set output, and the identification information, means that retrieves the retained use history information based on the read identification information, means that determines the lifespan of the probe based on the retrieved use history information, and means that outputs alert information indicating that the probe reaches the lifespan thereof when it is determined that the probe reaches the lifespan.

Further, U.S. Patent No. 2012/0078278 A1 as the second conventional example discloses a surgical system including a battery assembly with a control circuit provided in a housing, a handle assembly to which the battery assembly is detachably connected, and which includes an ultrasound dissection blade, and an ultrasound transducer and generating device (TAG) assembly. U.S. Patent No. 2012/0078278 A1 discloses the surgical system including means that measures use of the TAG assembly, and a content of determining whether or not the number of times of activation of the TAG assembly, and the time period until shutdown performed by an actual time clock circuit are the number of times and the time period which correspond to one time of actual use.

Further, U.S. Patent No. 2005/0070800 A1 as the third conventional example discloses a surgical system including a probe having a first storage section that stores determination reference information relating to abnormality determination, a hand piece having a second storage section that stores the determination reference information relating to abnormality determination and an ultrasound transducer, and a control device that determines presence or absence of abnormality of the surgical system based on a result of information reading processing of reading the determination reference information from the two storage sections, further determines presence or absence of abnormality of the surgical system based on the determination reference information which is read, and stops drive of the ultrasound transducer when the surgical system has abnormality.

SUMMARY OF THE INVENTION

A surgical system according to one aspect of the present invention has an ultrasound treatment instrument having an ultrasound transducer, a power supply apparatus to which the ultrasound treatment instrument is detachably connected, an energy supply section that is provided in the power supply apparatus, and supplies drive energy that causes the ultrasound transducer to be ultrasound-driven as output energy, a clock that is provided in the power supply apparatus, and measures a present time, a time updating section that is provided in the power supply apparatus, and outputs the present time, a storage section that is provided in the ultrasound treatment instrument, stores a final updated time as an updated time that is at least finally updated in the present time which is outputted from the time updating section, and stores a number of times of use of the ultrasound treatment instrument, a time period calculation section that calculates a non-connection time period in which the ultrasound treatment instrument and the power supply apparatus are not connected based on a difference between the final updated time which is stored in the storage section, and the present time by the clock, a comparison section that determines whether or not the non-connection time period which is calculated in the time period calculation section exceeds a predetermined time period, a processing section that performs processing of generating an update signal that causes the number of times of use to be updated in accordance with a result of determination with respect to a parameter including at least one of a number of times of output of the drive energy, an output time period of the drive energy, output power of the drive energy, an output current integrated value of the drive energy, an output voltage integrated value of the drive energy, an output power integrated value of the drive energy, a continuous output time period of the drive energy, an output time period integrated value of the drive energy, and a connection time period of the ultrasound treatment instrument and the power supply apparatus, when it is determined that the non-connection time period exceeds the predetermined time period in the comparison section, and a number of times of use updating section that updates the number of times of use based on the update signal.

BRIEF DESCRIPTION OF THE DRAWINGS

FIG. 6 is a flowchart showing a typical processing content of the first embodiment;

FIG. 8B is a flowchart showing a processing content in a case in which FIG. 8A is modified;

DETAILED DESCRIPTION OF THE PREFERRED EMBODIMENT

Hereinafter, an embodiment of the present invention will be described with reference to the drawings.

First Embodiment

Figure 1:
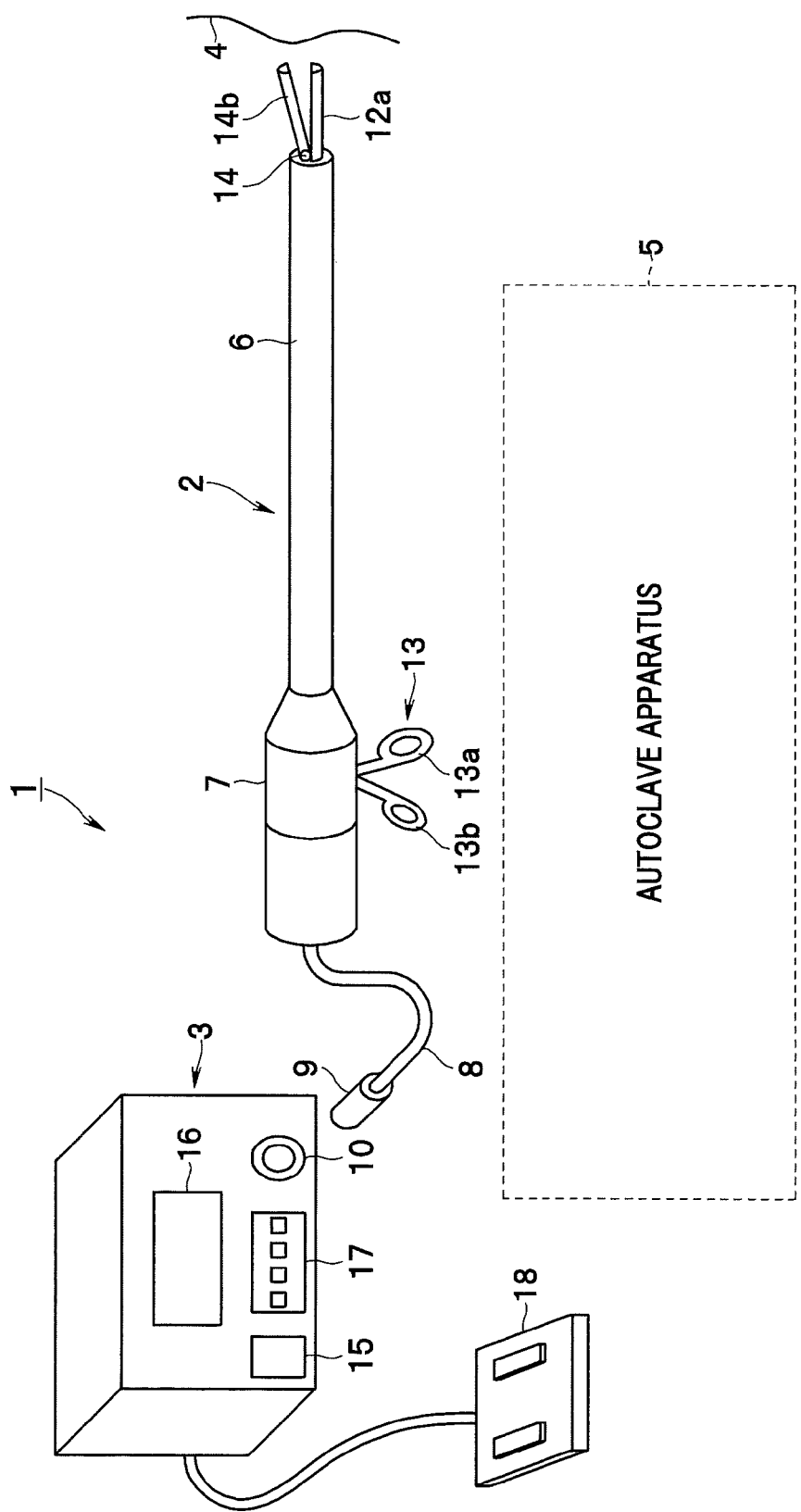
FIG. 1 is a perspective view showing a whole of a surgical system of a first embodiment of the present invention.

As shown in FIG. 1, a surgical system 1 of a first embodiment of the present invention has an ultrasound treatment instrument 2 for performing treatment by ultrasound vibration energy (abbreviated as ultrasound treatment) to living tissue 4 to be treated in a patient, and a power supply apparatus 3 to which the ultrasound treatment instrument 2 is detachably connected.

Note that the ultrasound treatment instrument 2 which has been used in ultrasound treatment to the living tissue 4 is accommodated in an accommodation chamber of an autoclave apparatus 5 shown by the dotted line, is subjected to sterilization treatment for a predetermined time period in an atmosphere of high-temperature and high-pressure steam in the accommodation chamber and set in a clean state, and is used as the ultrasound treatment instrument of the next time.

The ultrasound treatment instrument 2 has an elongated sheath 6, a hand piece 7 provided at a rear end (a proximal end) of the sheath 6, and a cable 8 that is extended from a rear end of the hand piece 7, and a connector 9 is provided at a terminal end of the cable 8. The connector 9 is detachably connected to a connector receptacle 10 of the power supply apparatus 3.

Figure 2:
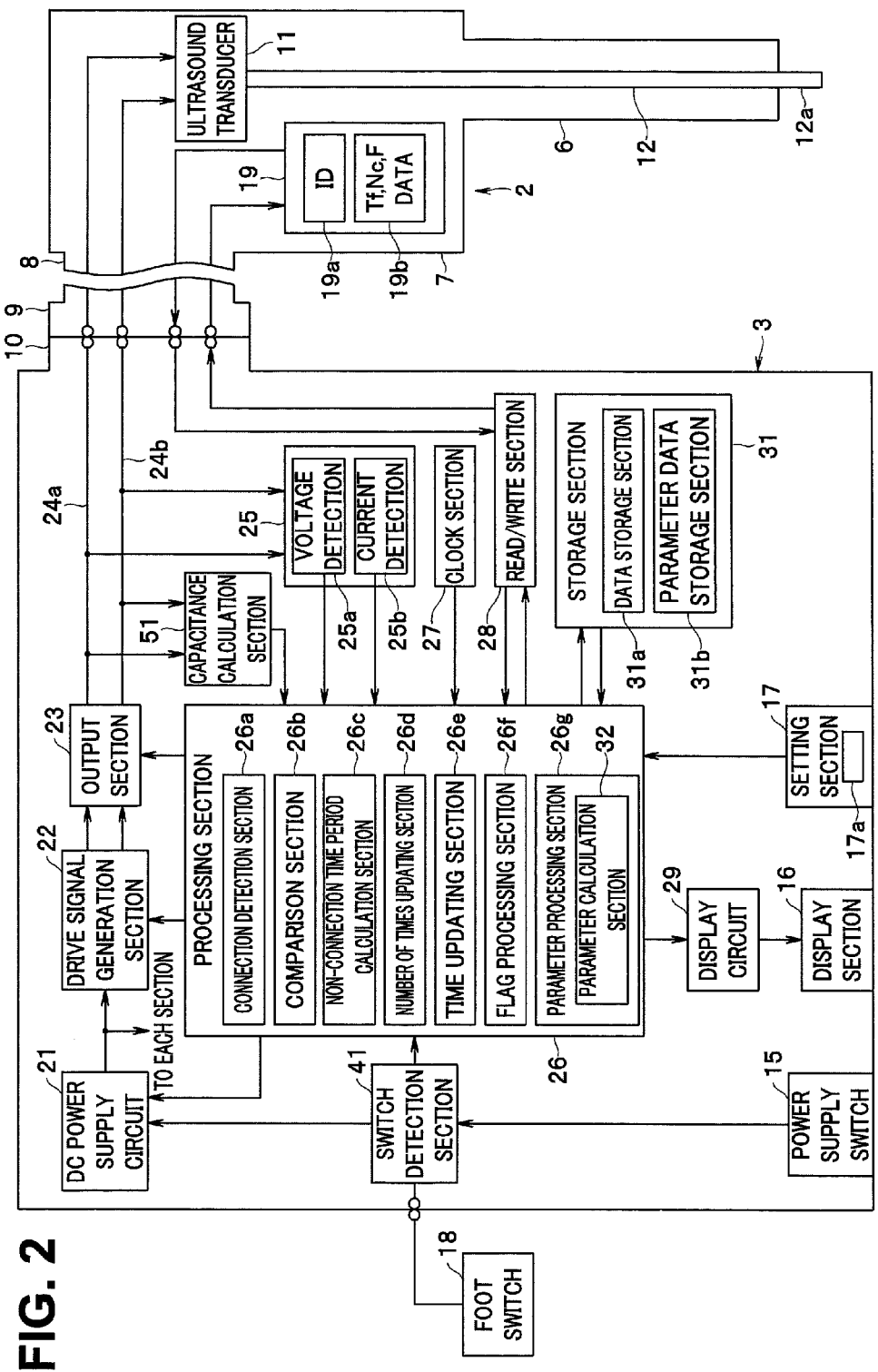
FIG. 2 is a block diagram showing an internal configuration of a power supply apparatus in the surgical system.

Further, inside the hand piece 7, an ultrasound transducer 11 is accommodated as shown in FIG. 2, and an ultrasound drive signal that (forms output energy or drive energy) is outputted from an output section 23 in the power supply apparatus 3 is supplied (applied) thereto, whereby the ultrasound transducer 11 performs ultrasound vibration in response to drive power (or output power) of the aforementioned ultrasound drive signal. The ultrasound vibration by the ultrasound transducer 11 is transmitted to a distal end side thereof by a probe 12 a proximal end of which is connected to a front end of the ultrasound transducer 11. Note that the ultrasound transducer 11 is configured by a Langevin transducer fastened with a bolt.

The probe 12 as an ultrasound vibration transmitting member that transmits ultrasound vibration is inserted through the sheath 6, and a distal end portion 12a of the probe 12 protrudes from a distal end of the sheath 6.

Further, as shown in FIG. 1, the hand piece 7 is provided with a grip portion 13 that protrudes to a lower end side, a surgeon is enabled to rotate a grasping portion 14b that is provided at a pivoted section 14 rotatably with respect to the distal end portion 12a which protrudes from the distal end of the sheath 6 by grasping the grip portion 13, and performing an operation of opening and closing finger rest portions 13a and 13b that configure the grip portion 13. Subsequently, the surgeon is enabled to perform ultrasound treatment such as dissection and coagulation by holding a site to be treated in the living tissue 4 with the distal end portion 12a of the probe 12 and the grasping portion 14b.

Further, as shown in FIG. 1, on a front surface of the power supply apparatus 3, a power supply switch 15 for turning ON/OFF the power supply, a display section 16 that performs display of an output current and the like, a setting section 17 that is used for performing an operation for setting an output level and various settings (selection) or the like, and the like are provided. Further, a foot switch 18 for the surgeon to perform an instruction operation of switching ON/OFF of an ultrasound output with a foot is connected to the power supply apparatus 3.

Further, as shown in FIG. 2, the ultrasound treatment instrument 2 has a first storage section (also simply called a storage section) 19 including an ID storage section 19*a* that stores identification information (abbreviated as ID or ID information) for identifying respective ultrasound treatment instruments 2, and a data storage section 19*b* that stores respective data of a final connection time (or a final updated time) Tf as a final time when the ultrasound treatment instrument 2 is connected to the power supply apparatus 3, a number Nc of cases of diseases that is counted as the number of times of use at which the ultrasound treatment instrument 2 is used for each case of a disease, and a count flag F as number of times update identification information which will be described later. In FIG. 2, the data storage section 19*b* is abbreviated as Tf, Nc, F data.

As shown in FIG. 2, the power supply apparatus 3 contains a DC power supply circuit 21 that converts a commercial power supply into a DC power supply, and the DC power supply circuit 21 outputs a DC power necessary for an operation to respective sections or circuits such as a drive signal generation section (or a drive signal generation circuit) 22.

The drive signal generation section 22 generates a drive signal of approximately several tens kHz to cause the ultrasound transducer 11 to perform ultrasound vibration, and outputs the drive signal to the output section (or the output circuit) 23. The output section 23 amplifies the drive signal from the drive signal generation section 22, and outputs (applies) the drive signal to the ultrasound transducer 11 as the ultrasound drive signal (hereinafter, abbreviated simply as a drive signal) which causes the ultrasound transducer 11 to perform ultrasound vibration.

Further, drive wires 24*a* and 24*b* that are outputted to the ultrasound transducer 11 from the output section 23 are connected to a detection section 25 including a voltage detection circuit 25*a* and a current detection circuit 25*b*. The voltage detection circuit 25*a* detects an output voltage (also simply called a voltage) of the drive signal which is outputted to the ultrasound transducer 11 in an effective value, for example, and the current detection circuit 25*b* detects an output current (also simply called a current) of the drive signal in an effective value, for example. Note that the voltage detection circuit 25*a* and the current detection circuit 25*b* are not limited to the case of detection in effective values. The voltage detection circuit 25*a* and the current detection circuit 25*b* output the voltage and the current of the drive signal which are detected, to a processing section 26.

The processing section 26 performs control and processing of operations of the DC power supply circuit 21, the drive signal generation section 22, the output section 23 and the like of the power supply apparatus 3.

Further, the power supply apparatus 3 has a clock circuit or a clock section 27 (as a clock) that measures a present time, and a read/write section 28 including a read circuit that performs read of ID in the aforementioned storage section 19 and read of data in the data storage section 19*b*, and a write circuit that performs write of data.

The clock section 27 outputs the present time measured by a clock with the clock to be a reference to the processing section 26, and the processing section 26 performs various kinds of processing and control synchronously with the clock.

Further, the processing section 26 has a function of a connection detection section 26*a* that performs processing of regularly reading ID from the storage section 19 via the read/write section 28 based on the present time or the like from the clock section 27, detecting that the ultrasound treatment instrument 2 is in a connected state connected to the power supply apparatus 3 when the connection detection section 26*a* reads the ID, and detecting that the ultrasound treatment instrument 2 is in a non-connected state in which the ultrasound treatment instrument 2 is not connected to the power supply apparatus 3 when the connection detection section 26*a* cannot read the ID.

Note that besides means that detects presence or absence of connection of the ultrasound treatment instrument 2 to the power supply apparatus 3 based on whether. ID can be read or not, connection detection pins Ca, Ca', Cb and Cb' that detect presence or absence of connection are provided as shown in FIG. 4, whereby a connection detection section 51 that mechanically detects presence or absence of connection of the ultrasound treatment instrument 2 to the power supply apparatus 3 may be configured.

Figure 4:
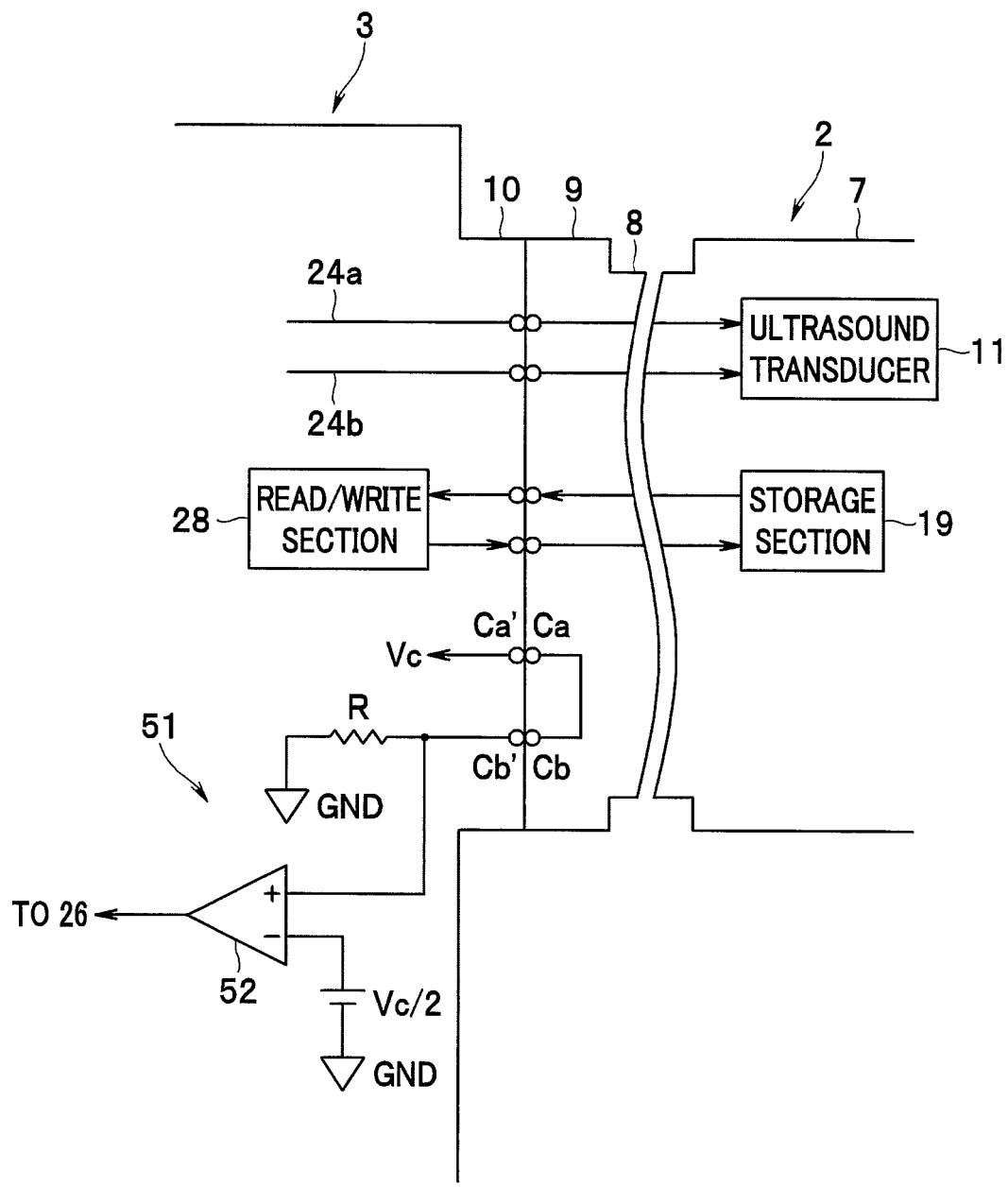
FIG. 4 is a diagram showing a configuration in a case in which detection of connection of an ultrasound treatment instrument to the power supply apparatus is performed with use of a connection detecting pin.

As shown in FIG. 4, the connector 9 is provided with the connection detection pins Ca and Cb which are electrically continued by a conductor wire, and the connector receptacle 10 is provided with the connection detection pins Ca' and Cb' to which the connection detection pins Ca and Cb are respectively connected. The connection detection pin Ca' is connected to a power supply terminal that outputs a predetermined voltage Vc, and the connection detection pin Cb' is connected to a ground GND via a resistance R, and is connected to a noninverting input terminal of a comparator 52.

Further, a voltage of Vc/2, for example, is applied to the noninverting input terminal of the comparator 52. The comparator 52 outputs a detection signal of a low level (an L level) in the non-connection state in which the ultrasound treatment instrument 2 is not connected to the power supply apparatus 3, and a detection signal of a high level (an H level) in the connection state in which the ultrasound treatment instrument 2 is connected, to the processing section 26.

Further, when the processing section 26 detects that the state is changed to the connection state from the non-connection state by the connection detection section 26*a* or the like, the processing section 26 reads the final connection time (or the final updated time) Tf, the number Nc of cases of diseases, and the count flag F from the data storage section 19*b* of the storage section 19 in the ultrasound treatment instrument 2 which is detected as being connected via the read/write section 28.

Further, the processing section 26 has a function of a comparison section (or a determination section) 26*b* that compares whether or not the number Nc of cases of diseases as the number of times of use which is read from the storage section 19 is equal to or smaller than a first number of cases of diseases threshold value Nα that is set in advance as a maximum number of times of use or a number of endurable times corresponding to a lifespan of the ultrasound treatment instrument 2 storing the number Nc of cases of diseases, and whether or not the number Nc of cases of diseases is equal to or smaller than a second number of cases of diseases threshold value Nβ which is smaller than the first number of cases of diseases threshold value Nα by at least about several times (may be set to one time).

Further, in a case of a comparison result that the number Nc of cases of diseases read from the storage section 19 exceeds the first number of cases of diseases threshold value Nα, the comparison section 26*b* outputs information of the comparison result that the number Nc exceeds the first number of cases of diseases threshold value Nα to the display section 16 via a display circuit 29. Subsequently, the display section 16 notifies a user that the number Nc of cases of diseases exceeds the number of endurable times corresponding to the lifespan, for example.

Further, in a case of a comparison result that the number Nc of cases of diseases which is read from the storage section 19 exceeds the second number of cases of diseases threshold value Nβ, the comparison section 26b outputs information of the comparison result that the number Nc exceeds the second number of cases of diseases threshold value Nβ to the display section 16 via the display circuit 29. Subsequently, the display section 16 notifies the user that the number of times of use is in a state of exceeding the second number of cases of diseases threshold value Nβ, or that the ultrasound treatment instrument can be used in the future only a very small number of times until the number of endurable times corresponding to the lifespan.

Accordingly, the display section 16 has a function of a notification section that notifies the user of the content corresponding to a comparison result in the case of the comparison result that the number Nc of cases of diseases which is read from the storage section 19 exceeds the first number of cases of diseases threshold value Nα or the second number of cases of diseases threshold value Nβ. Note that the display section 16 also displays drive power and the like detected by the detection section 25.

Further, the processing section 26 has a function of a non-connection time period calculation section 26c (as a time period calculation section) that calculates a non-connection time period Tnc (=Tp−Tf) that is a difference from a present time Tp when the final connection time Tf is read, when the final connection time Tf is read from (the data storage section 19b of) the storage section 19.

The non-connection time period calculation section 26c calculates a non-connection time period from a time when the ultrasound treatment instrument 2 is detached from the power supply apparatus 3 at the previous time (the time is substantially equal to the final connection time Tf) to the present time Tp when reading the time by being connected by the connection operation of this time.

The processing section 26 has a function of a number of times updating section 26d as a number of times of use updating section that compares whether or not the non-connection time period Tnc which is calculated by the non-connection time period calculation section 26c is equal to or, larger than a non-connection time period threshold value Tth set in advance, in the comparison section 26b, and performs processing of updating the above described number Nc of cases of diseases to increase the number Nc of cases of diseases by one, or not updating the above described number Nc of cases of diseases.

Further, the non-connection time period calculation section 26c also has a function of an elapsed days and time period calculation section that calculates elapsed days and time period Tc until the present time Tp as a date and time when the ultrasound treatment instrument 2 is connected to the power supply apparatus 3 first after a shipping date and time Tm as described in FIG. 13 that will be described later. The elapsed days and time period calculation section may be provided as a separate piece from the non-connection time period calculation section 26c.

Note that non-connection time period threshold value Tth is retained (stored) in a data storage section 31a in a second storage section (also simply called as a storage section) 31 that is provided in the power supply apparatus 3, for example, by being correlated with an ID of the ultrasound treatment instrument 2 or ultrasound transducer data in the ID.

The comparison section 26b uses the corresponding non-connection time period threshold value Tth via the read/write section 28 based on the ID of the ultrasound treatment instrument 2 which is connected to the power supply apparatus 3. Further, in the data storage section 31a in the storage section 31, the aforementioned first number of cases of diseases threshold value Nα and the second number of cases of diseases threshold value Nβ are retained (stored) by being correlated with the ID of the ultrasound treatment instrument 2 or the ultrasound transducer data in the ID.

Note that the non-connection time period threshold value Tth, the first number of cases of diseases threshold value Nα and the second number of cases of diseases threshold value Nβ may be retained (stored) in the storage sections 19 at the respective ultrasound treatment instruments 2 sides, instead of being retained in the storage section 31 at the power supply apparatus 3 side.

Further, the processing section 26 has a function of a time updating section 26e that regularly updates the present time of the past which is stored in the data storage section 19b of the storage section 19 as an updated time, in the same way as the connection detection section 26a regularly performs connection detection.

Namely, in the ultrasound treatment instrument 2, in the connected state in which the ultrasound treatment instrument 2 is connected to the power supply apparatus 3, the present time which is stored in the data storage section 19b in the storage section 19 is regularly updated (overwritten) by the time updating section 26e each time a set time period that is set in advance elapses. Subsequently, when the ultrasound treatment instrument 2 in the connected state is detached from the power supply apparatus 3, the present time which is updated and stored immediately before the ultrasound treatment instrument 2 is detached comes to be the final connection time Tf.

As above, the time updating section 26e regularly updates the present time of the past which is stored in the data storage section 19b of the storage section 19 to a new present time via the read/write section 28, based on the present time from the clock section 27. In the present embodiment, the final connection time Tf is enabled to be detected, and the non-connection time period Tnc is enabled to be calculated.

Further, the processing section 26 has a function of a flag processing section 26f for updating the number Nc of cases of diseases precisely by preventing failure to count the number of cases of diseases with respect to a case in which the non-connection time period Tnc which is calculated by the non-connection time period calculation section 26c is short.

The flag processing section 26f performs processing of updating the number Nc of cases of diseases, and updating a count flag F (as the identification information on the number Nc of cases of diseases being updated) to one, when a calculation value of a parameter (also described as a parameter calculation value) that is set as described as follows exceeds a parameter threshold value, for example. The case of the flag state in which the count flag F is one as described above corresponds to (number of times update) identification information expressing that the number Nc of cases of diseases is updated. In contrast with this, a case of a flag state in which the count flag F is zero corresponds to (number of times update) identification information expressing that the number Nc of cases of diseases is not updated.

Further, the processing section 26 has a mechanism of a parameter processing section 26g that prepares various parameters relating to evaluation of a lifespan or count (counting) of the number Nc of cases of diseases so as to be able to precisely count the number Nc of cases of diseases at which the ultrasound treatment instrument 2 is practically used, and performs processing of update/non-update of the number Nc of cases of diseases by using a parameter which is selected or set. When the parameter processing section 26 updates the number Nc of cases of diseases as the number of times of use, the parameter processing section 26 generates (produces) an update signal, and outputs the generated update signal to the number of times updating section 26d as the number of times of use updating section, and the number of times updating section 26d updates the number Nc of cases of diseases to increase the number Nc of cases of diseases by one. Further, when the parameter processing section 26 does not update the number Nc of cases of diseases as the number of times of use, the parameter processing section 26 does not generate (produce) an update signal.

Further, for example, the setting section 17 is provided with a parameter setting section (or a parameter selecting section) 17a that selects or sets a parameter to be used to count the number Nc of cases of diseases. When an operator or the like sets or selects one parameter from a plurality of parameters by the parameter setting section 17a, the parameter setting section 17a sends information on the parameter which is set or selected to the parameter processing section 26g of the processing section 26.

The parameter processing section 26g has a parameter calculation section 32 that calculates (detects) various parameters so as to be able to perform processing of update/non-update of the number Nc of cases of diseases by using (the calculation value) of the parameter which is set or selected.

Figure 5:
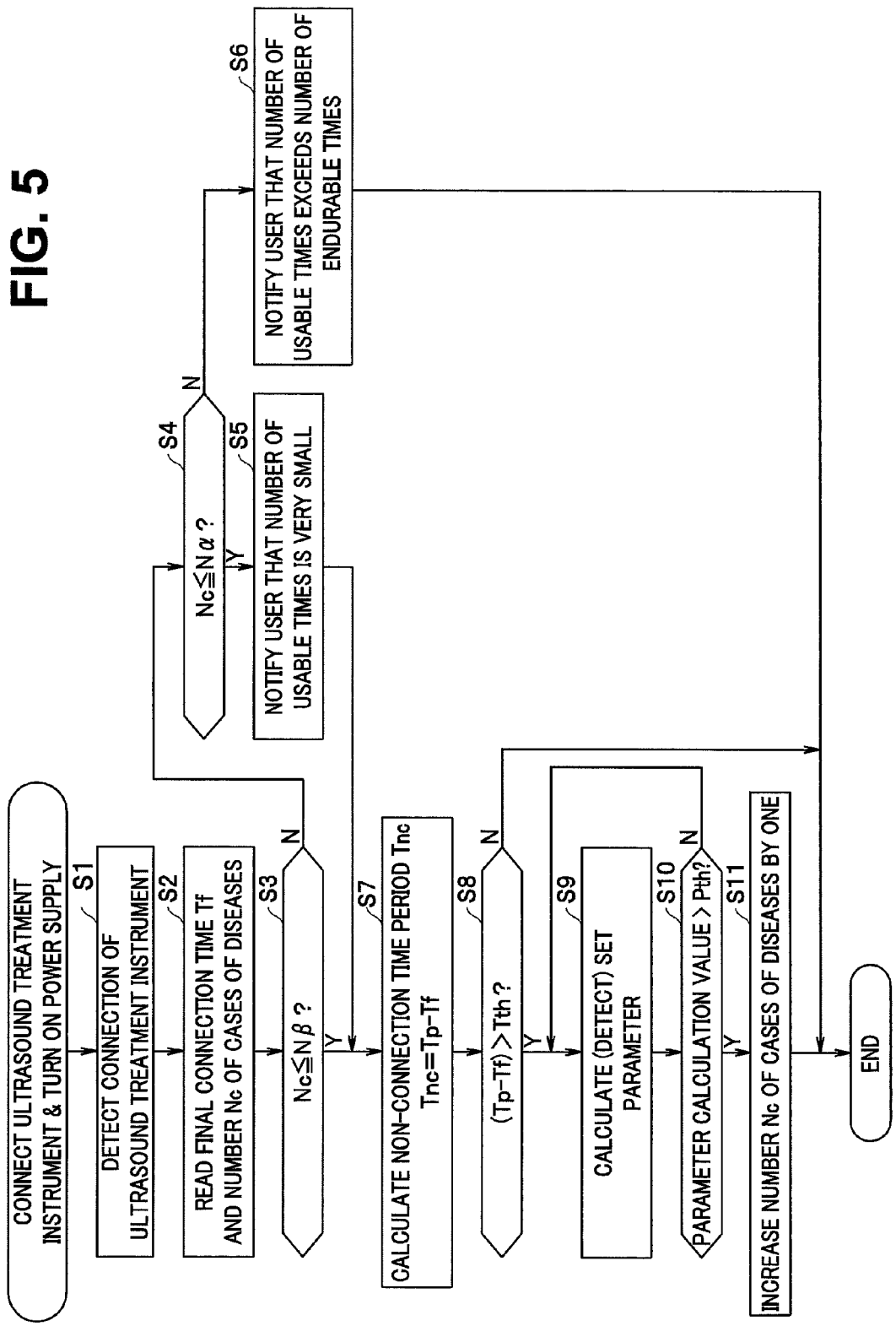
FIG. 5 is a flowchart showing a basic processing content of the present invention.
Figure 7A:
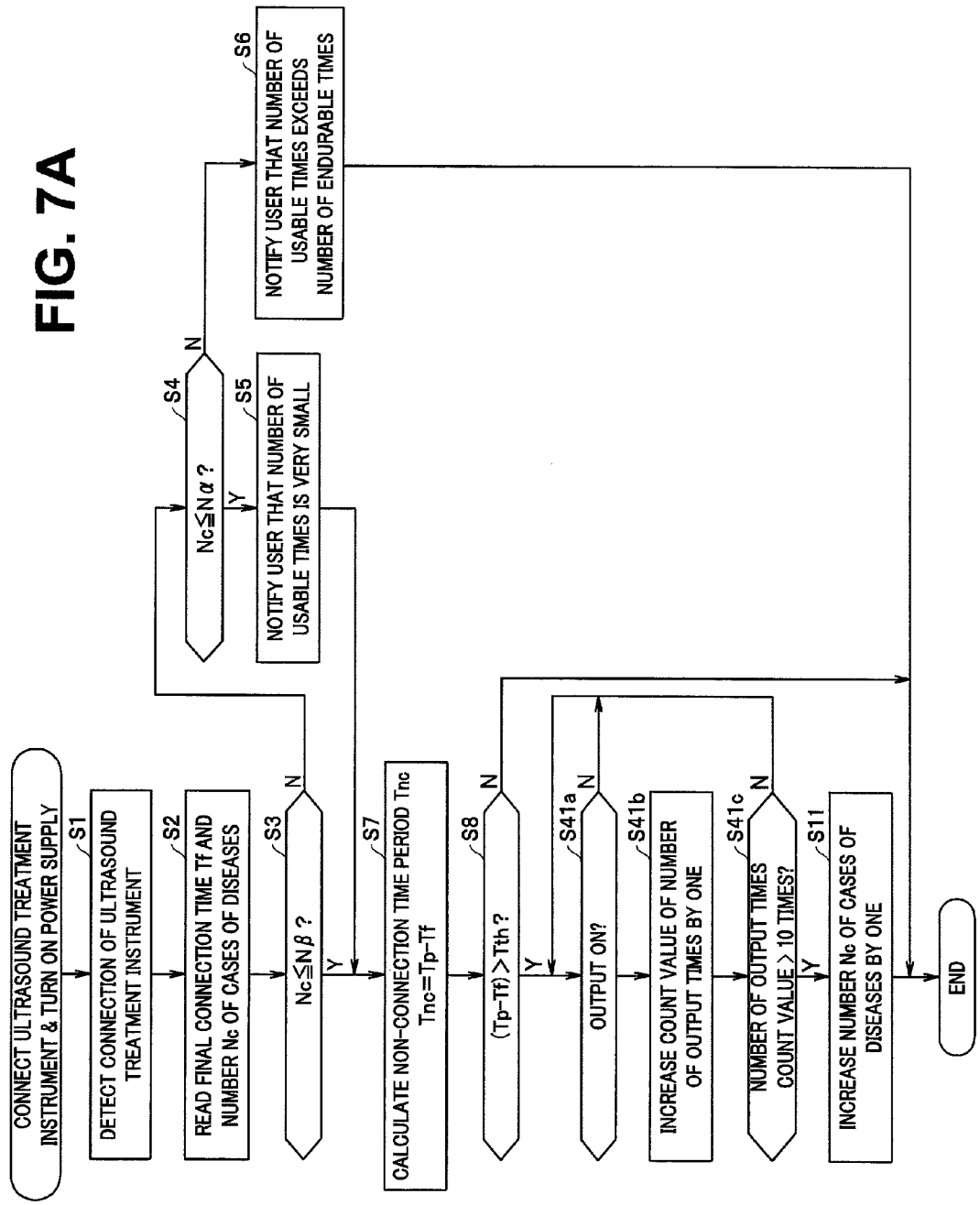
FIG. 7A is a flowchart showing the processing content in FIG. 5 in a case of a set parameter is the number of output times.
Figure 7B:
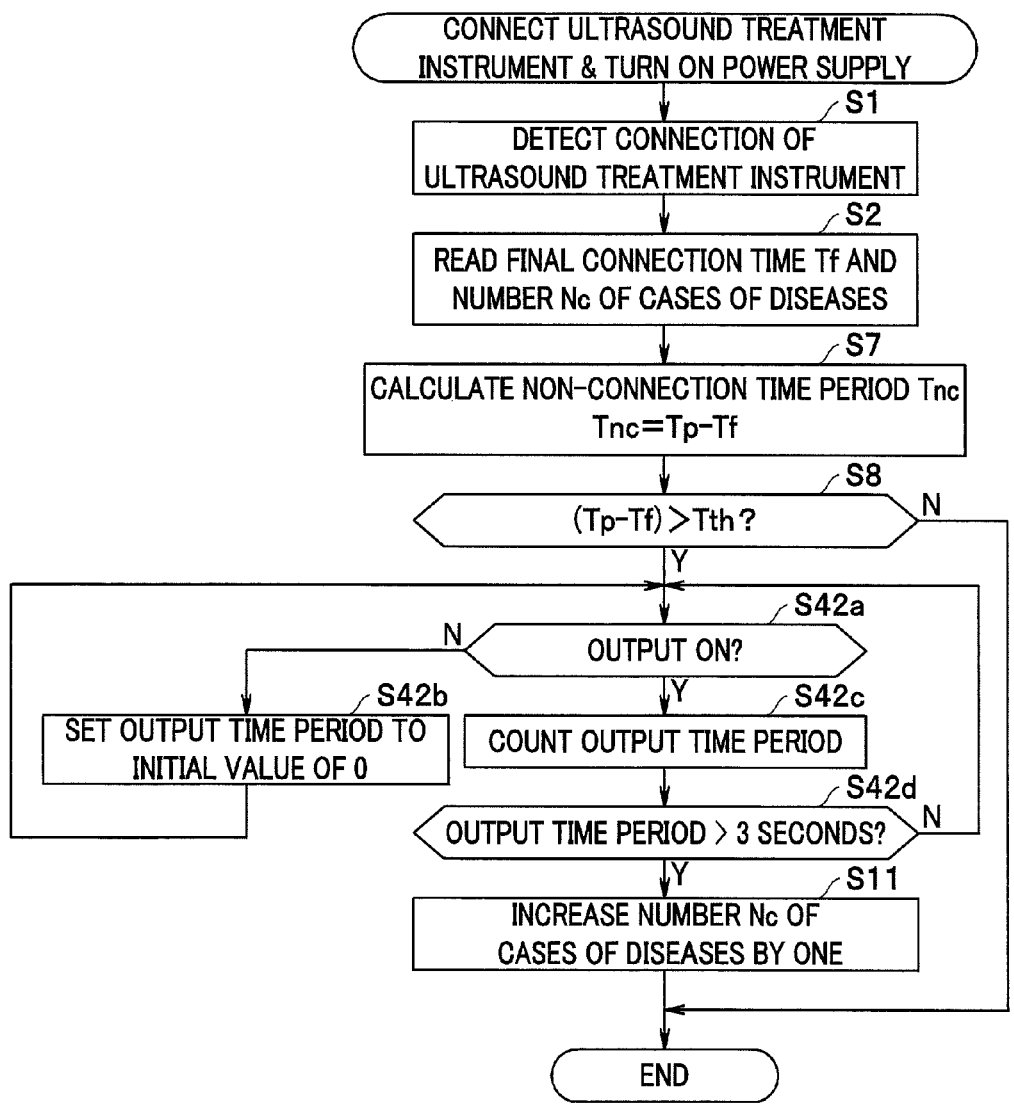
FIG. 7B is a flowchart showing a processing content from which part of the processing in FIG. 5 is omitted in a case in which the set parameter is a continuous output time period.
Figure 7C:
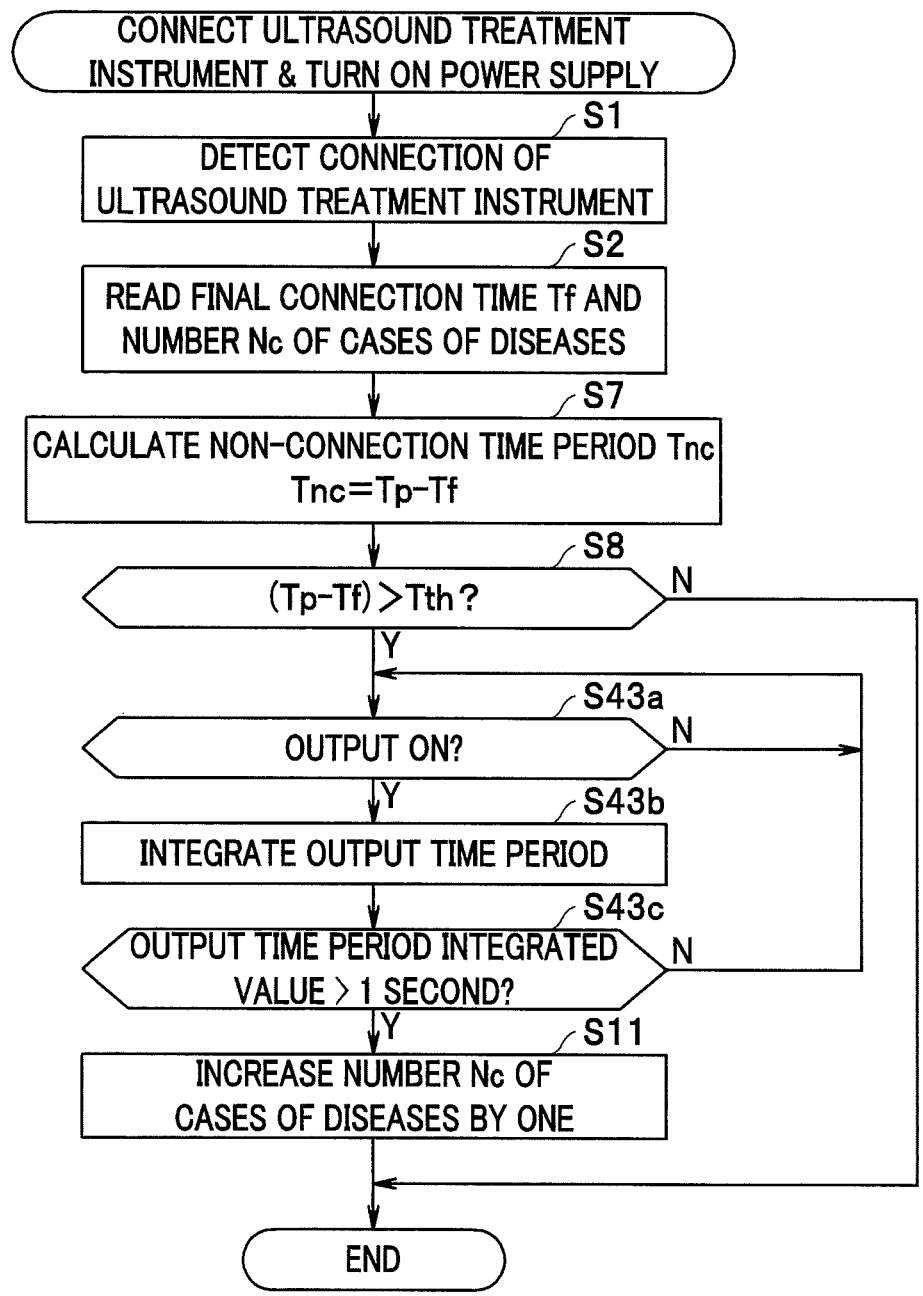
FIG. 7C is a flowchart showing a processing content from which part of the processing in FIG. 5 is omitted in a case in which the set parameter is an output time period integrated value.
Figure 7D:
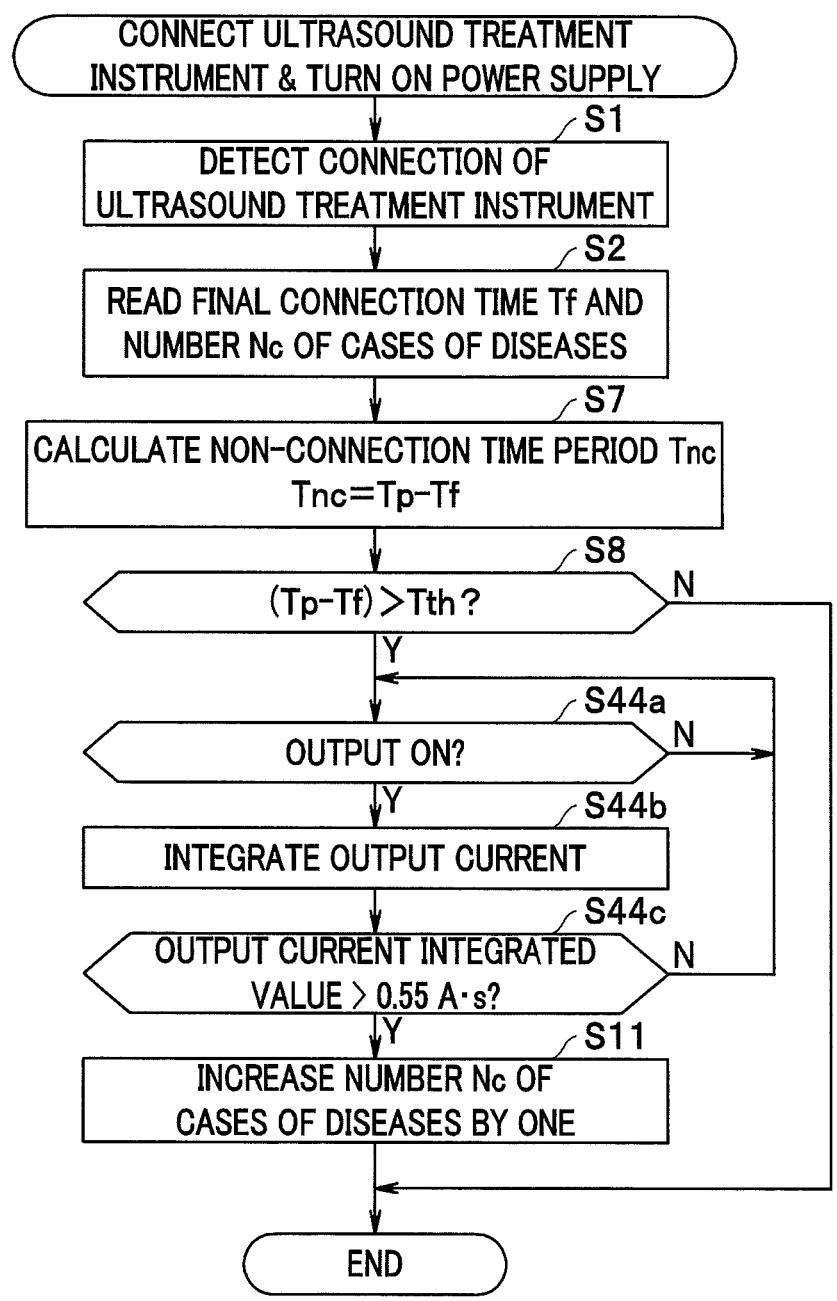
FIG. 7D is a flowchart showing a processing content from which part of the processing in FIG. 5 is omitted in a case in which the set parameter is an output current integrated value.
Figure 7E:
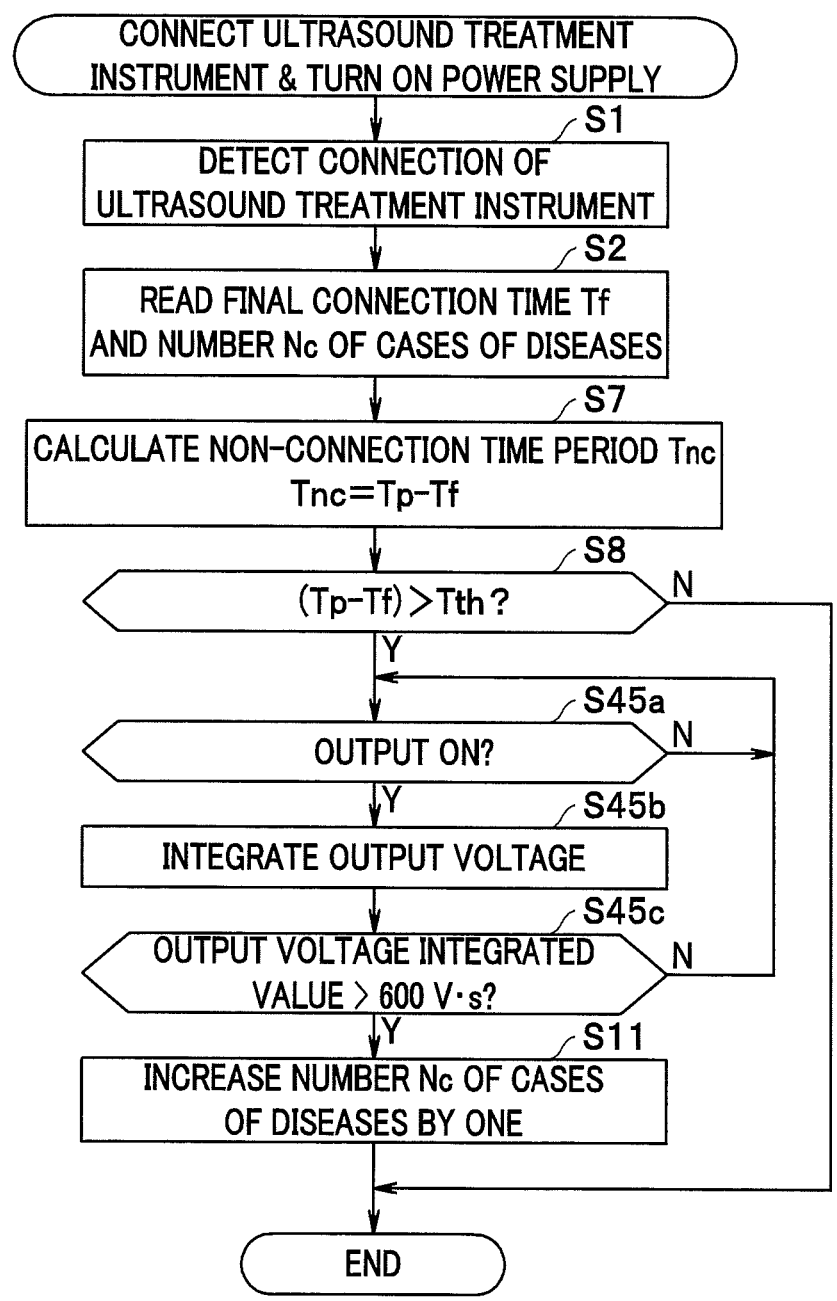
FIG. 7E is a flowchart showing a processing content from which part of the processing in FIG. 5 is omitted in a case in which the set parameter is an output voltage integrated value.
Figure 7F:
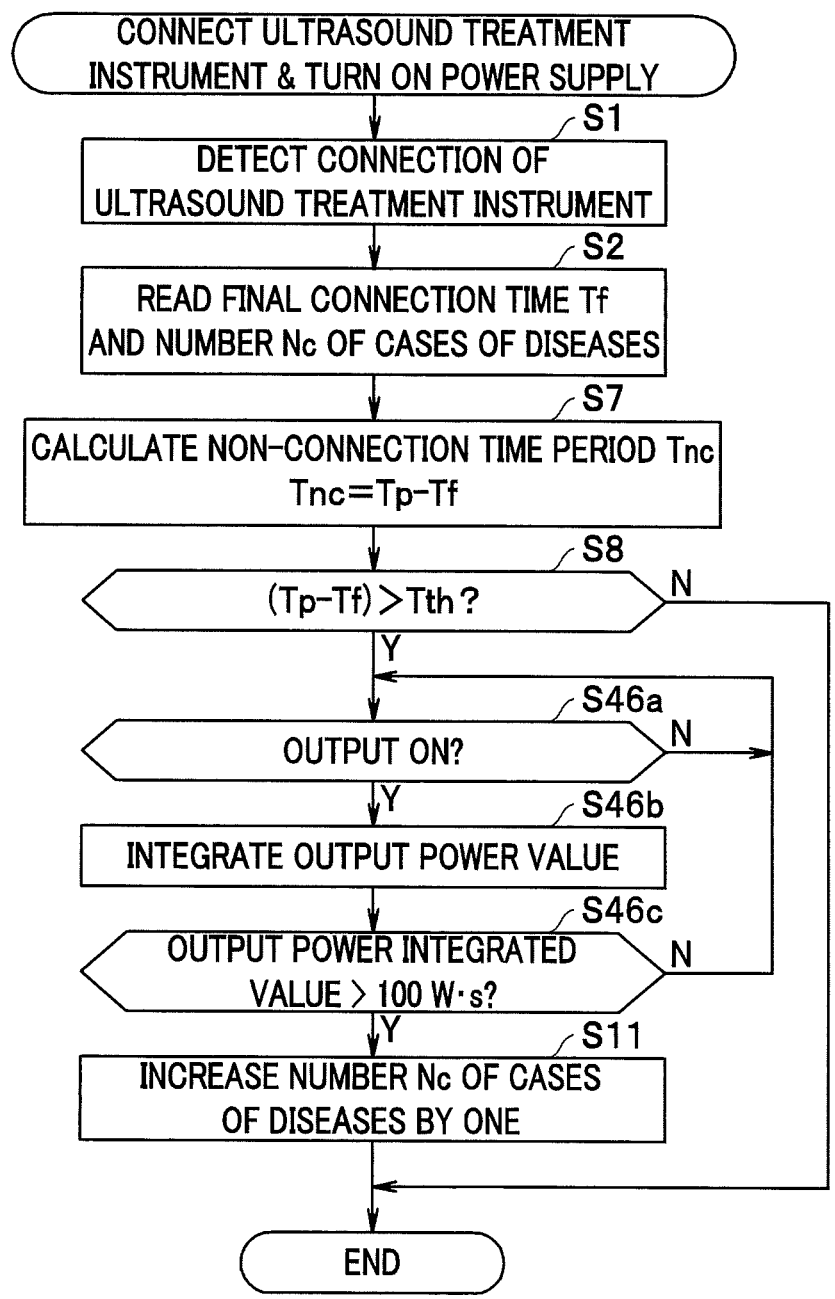
FIG. 7F is a flowchart showing a processing content from which part of the processing in FIG. 5 is omitted in a case in which the set parameter is an output power integrated value.
Figure 7G:
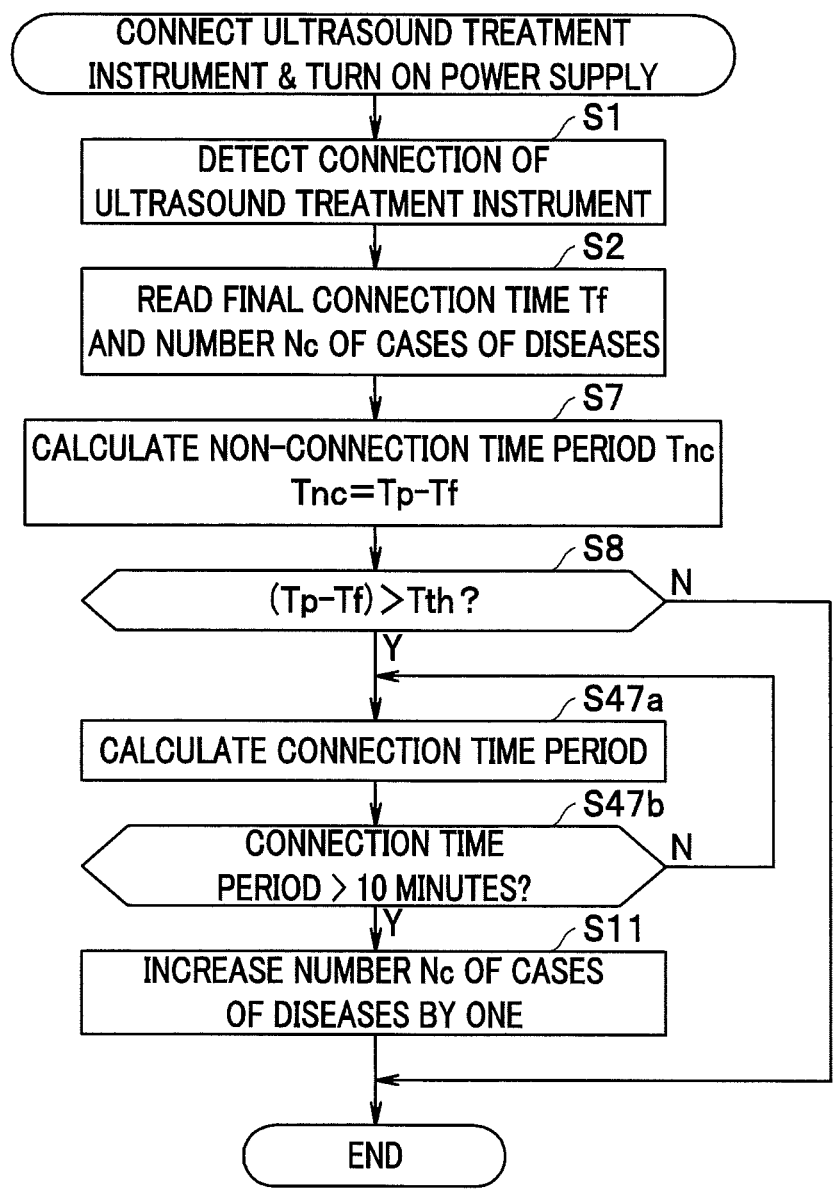
FIG. 7G is a flowchart showing a processing content from which part of the processing in FIG. 5 is omitted in a case in which the set parameter is a connection time period.
Figure 7H:
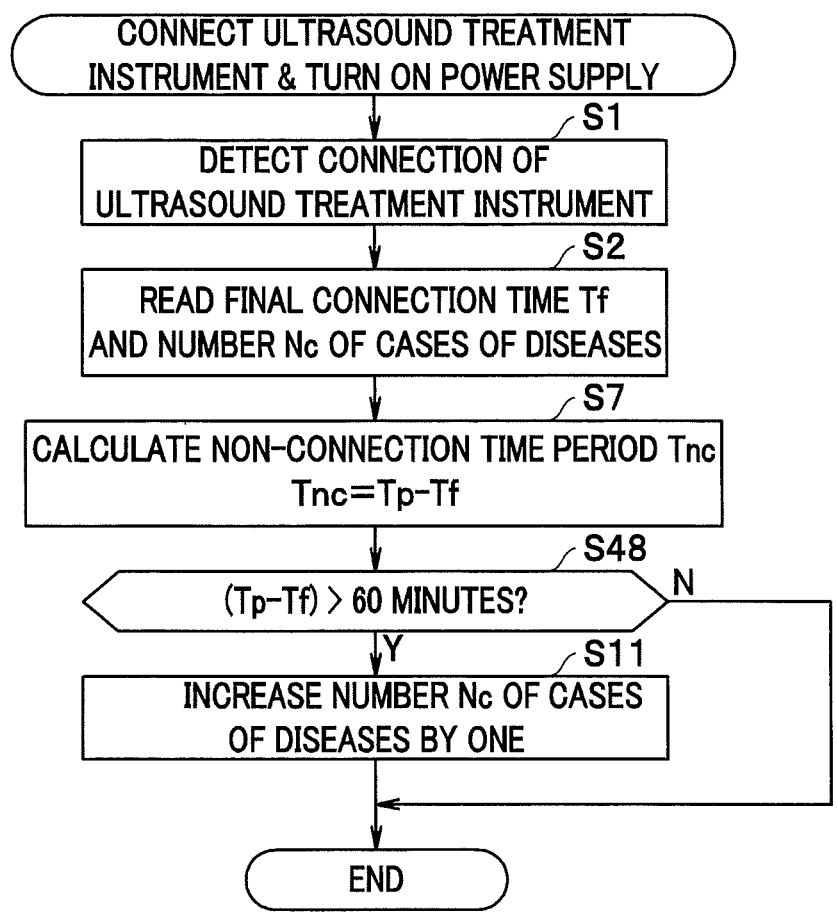
FIG. 7H is a flowchart showing a processing content of determining presence or absence of update of a number of cases of diseases based on whether or not a non-connection time period exceeds a non-connection time period threshold value.

In the present invention, it may be determined whether or not the number Nc of cases of diseases is updated from the calculation value of the non-connection time period Tnc by processing as shown in FIG. 5 and FIG. 7H as processing of a basic configuration. Namely, when the calculated non-connection time period (Tp−Tf) does not exceed the non-connection time period threshold value Tth, the number Nc of cases of diseases is not updated (an update signal for updating the number Nc of cases of diseases is not outputted to the number of times updating section 26d), and in contrast with this, when the calculated non-connection time period (Tp−Tf) exceeds the non-connection time period threshold value Tth, the update signal for updating the number Nc of cases of diseases may not be caused to be generated.

However, when the calculated non-connection time period (Tp−Tf) exceeds the non-connection time period threshold value Tth, such a case can occur that the ultrasound treatment instrument 2 is temporarily connected to the power supply apparatus 3, and thereafter, connection is ended without treatment being performed (in other words, without the ultrasound treatment instrument 2 being used in a case of a disease). In the case like this, it is determined whether or not drive power or the like as a parameter is outputted to the ultrasound transducer 11 of the ultrasound treatment instrument 3, whereby whether or not the ultrasound treatment instrument is used in treatment can be determined precisely. Further, frequency of use of the drive power, the power value and the like (mainly become factors of deteriorating the ultrasound transducer 11, and) relate to the lifespan of the ultrasound treatment instrument 2.

Therefore, in the present embodiment, besides the determination result with respect to the calculated non-connection time period (Tp−Tf), a parameter for determining whether or not the ultrasound treatment instrument is used in treatment is prepared, and whether or not to update the number Nc of cases of diseases is determined with use of the determination result of whether or not the parameter exceeds a threshold value (namely, a parameter threshold value) that is set for the parameter.

More specifically, in a case in which the calculated non-connection time period (Tp−Tf) exceeds the non-connection time period threshold value Tth, the case is regarded as an update candidate state which has a possibility of updating the number Nc of cases of diseases, the parameter is further calculated (detected) in the update candidate state, and in a case of a determination result that the parameter calculation value exceeds the parameter threshold value, the number Nc of cases of diseases is updated.

In contrast with this, in a case of a determination result that the parameter calculation value does not exceed the parameter threshold value, the number Nc of cases of diseases is not updated. The processing like this is performed, whereby the number Nc of cases of diseases can be counted more precisely. In other words, the surgical system 1 which can detect the lifespan of the ultrasound treatment instrument 2 more precisely is realized.

Figure 3:
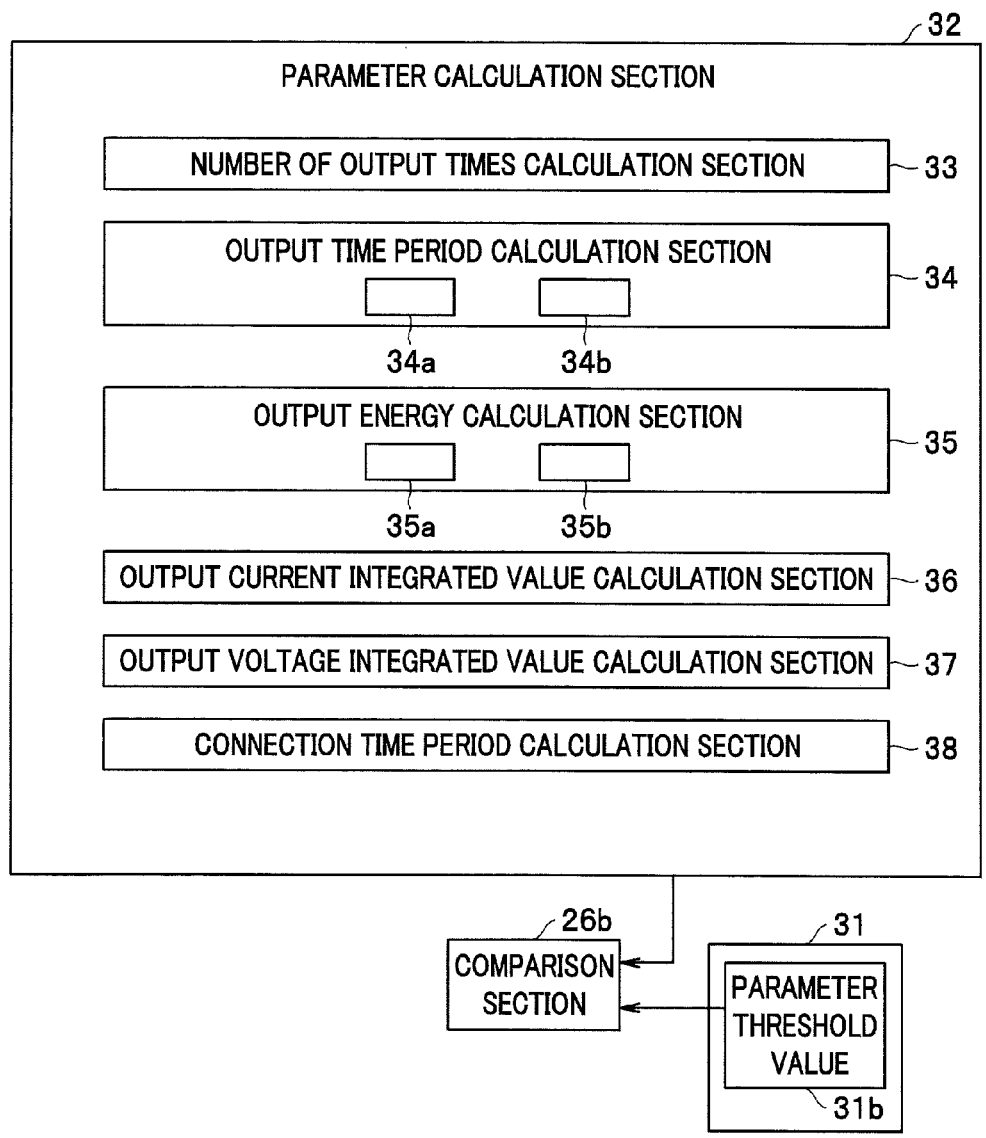
FIG. 3 is a block diagram showing a configuration of a parameter processing section in FIG. 2.

FIG. 3 shows a configuration of the parameter calculation section 32 which calculates various parameters for use in evaluation of the lifespan (or determination of update of the number Nc of cases of diseases).

The parameter calculation section 32 has a number of output times calculation section 33, an output time period calculation section 34 and an output power calculation section (or an output energy calculation section) 35 that respectively calculate (or measure) a number of output times at which a drive signal is actually outputted to the ultrasound transducer 11 from the output section 23 which configures an energy supply section, an output time period, and drive power (output power), in the connected state in which the ultrasound treatment instrument 2 is connected to the power supply apparatus 3. Note that the output power calculation section 35 calculates the drive power or the output power, but the drive power or the output power corresponds to output energy, and therefore, the output power calculation section 35 also can be called the output energy calculation section.

Further, the parameter calculation section 32 has an output current integrated value calculation section (or a current integrated value calculation section) 36 and an output voltage integrated value calculation section (or a voltage integrated value calculation section) 37 that respectively calculate (or measure) an output current integrated value (or a current integrated value) and an output voltage integrated value (or a voltage integrated value) of the drive signal which is outputted to the ultrasound transducer 11 in the above described connected state in effective values, and a connection time period calculation section 38 that calculates (or measures) a connection time period as a time period of the connected state.

The above described output time period calculation section 34 has two functions of a continuous output time period calculation section 34a that calculates a continuous output time period in which the drive signal is continuously (not intermittently) outputted as the aforementioned output time period, and an output time period integrated value calculation section 34b that calculates an integrated value of the output time period, in the above described connected state.

Further, the output power calculation section 35 has functions of a first output power calculation section 35a that calculates instantaneous output power (amount), and an output power integrated value calculation section 35b as a second output power calculation section that calculates an integrated value of output power, in the above described connected state.

The parameter calculation section 32 outputs a calculation value of a parameter, which is actually selected from the number of output times, the output time period, the output power, the output current integrated value, the output voltage integrated value and the connection time period as the plurality of parameters, to the comparison section 26b. The comparison section 26b reads the parameter threshold value data (illustrated in FIG. 3) as the parameter threshold value corresponding to the calculation value of the selected parameter from a parameter data storage section 31b that is stored (retained) in the storage section 31 in advance, and compares the parameter threshold value with the calculation value of the parameter.

In the above described parameter data storage section 31b, a number of output times threshold value, an output time period threshold value, an output power threshold value, an output current integrated value threshold value, an output voltage integrated value threshold value and a connection time period threshold value as respective threshold values of the number of output times, the output time period, the output power, the output current integrated value, the output voltage integrated value and the connection time period as the parameters are retained. For example, the number of output times threshold value, the continuous output time period threshold value, the output time period integration threshold value, the output power integration threshold value, the output current integrated value threshold value, the output voltage integrated value threshold value and the connection time period threshold value are respectively set to 10 times, three seconds, one minute, 100 W·s (an effective value), 0.5 A·s (an effective value), and 600 V·s (an effective value).

When the parameters from the number of output times to the connection time period described above are expressed by P1 to P6, for example, and a threshold value corresponding to a calculation value Pic of a parameter Pi (i=1 to 6) which is actually used is set as Pith, for example, the number Nc of cases of diseases is not updated when Pic≤Pith is satisfied, and the number Nc of cases of diseases is updated to be increased by one (that is, Nc+1) when Pic≤Pith is not satisfied (namely, in a case of Pic>Pith).

As above, the parameter processing section 26g in the processing section 26 performs processing of outputting an update signal for causing the number Nc of cases of diseases to be updated to be increased by one to the number of times updating section 26d, or not performing update and causing the number Nc of cases of diseases to remain as it is (not outputting the update signal), in accordance with the comparison result (the determination result) by the comparison section 26b, namely, processing of update/non-update of the number Nc of cases of diseases. Note that FIG. 2 shows the configuration example in which the parameter processing section 26g performs processing of update/non-update of the number Nc of cases of diseases by using the comparison section 26b outside the parameter processing section 26g, but a function corresponding to the comparison section 26b may be provided inside the parameter processing section 26g, and the parameter processing section 26g may perform comparison (determination) inside, and perform processing of update/non-update of the number Nc of cases of diseases.

Further, a function of the comparison section 26b may be provided inside (the number of output times calculation section 33 or the like of FIG. 3) the parameter calculation section 32 in the parameter processing section 26g, and the parameter calculation section 32 may compare (determine) whether or not the parameter calculation value calculated by the parameter calculation section 32 exceeds the parameter threshold value in the internal comparison section (without using the external comparison section 26b).

Further, the configurations shown in FIG. 2 and FIG. 3 show only specific examples, and configurations different from the configuration examples shown in FIG. 2 and FIG. 3 may be adopted. For example, one or a plurality of components in the connection detection section 26a, the comparison section 26b, the non-connection time period calculation section 26c, . . . , and the parameter processing section 26g which configure the processing section 26 shown in FIG. 2 may be configured outside the processing section 26, or to be separate from the processing section 26. Further, many of the respective functions in the processing section 26 in FIG. 2 can be configured through software by using a central processing unit (CPU), for example, but may be configured by exclusive hardware.

Further, the power supply apparatus 3 has a switch detection section 41 that detects ON/OFF of the power supply switch 15, and ON/OFF of output of a drive signal by the foot switch 18, the switch detection section 41 sends a detection signal of ON/OFF to the processing section 26, and the processing section 26 performs control processing corresponding to the detection signal.

For example, when the power supply switch 15 is turned ON, and thereafter is turned OFF, the DC power supply circuit 21 is stopped so that the DC power supply circuit 21 is caused not to output DC power supply based on a detection signal of OFF by the switch detection section 41. Note that when the power supply switch 15 is turned ON from an OFF state, the DC power supply circuit 21 is turned ON (to cause the DC power supply circuit 21 to output DC power supply) by bypassing the switch detection section 41, by an ON operation of the power supply switch 15.

Further, when a switch operation of ON to output is performed by the foot switch 18, control is performed so that a drive signal is outputted to the ultrasound transducer 11 from the output section 23, based on a detection signal of turning on output by the switch detection section 41. Further, when a switch operation of turning off output is performed by the foot switch 18, control is performed so that the drive signal is not outputted to the ultrasound transducer 11 from the output section 23 (namely, output is stopped).

The surgical system 1 of the configuration as above has the ultrasound treatment instrument 2 having the ultrasound transducer 11, the power supply apparatus 3 to which the ultrasound treatment instrument 2 is detachably connected, the output section 23 that is provided in the power supply apparatus 3, and configures the energy supply section which supplies drive energy that causes the ultrasound transducer 11 to perform ultrasound drive, the clock section 27 which is provided in the power supply apparatus 3, and configures the clock which measures a present time, the time updating section 26e which is provided in the power supply apparatus 3, and regularly outputs the present time as an updated time to be updated, the storage section 19 which is provided in the ultrasound treatment instrument 2, stores the final updated time as the updated time which is at least finally updated in the present time which is regularly outputted from the time updating section 26e, and stores the number Nc of cases of diseases as the number of times of use of the ultrasound treatment instrument 2, the non-connection time period calculation section 26c as the time period calculation section which calculates the non-connection time period in which the ultrasound treatment instrument 2 and the power supply apparatus 3 are not connected based on the difference between the final updated time stored in the storage section 19 and the present time by the clock, the processing section 26 which determines whether or not the non-connection time period exceeds a predetermined time period, and performs processing of generating the update signal which causes the number of times of use to be updated in accordance with the result of the determination with respect to the parameter relating to the lifespan of the ultrasound transducer 11 at least when it is determined that the non-connection time period exceeds the predetermined time period, and the number of times updating section 26d as the number of times of use updating section which updates the number of times of use in response to generation of the update signal.

Next, an operation of the present embodiment will be descried. In the following explanation, a case of performing connection detection by using the connection detection section 26a will be described, but the connection detection section 51 may be used. FIG. 5 shows a basic processing operation of the present invention. A user such as a surgeon connects the ultrasound treatment instrument 2 to the power supply apparatus 3, and turns on the power supply switch 15.

Thereupon, the respective sections in the power supply apparatus 3 are brought into an operation state, and in first step S1, the connection detection section 26a of the processing section 26 reads ID in the storage section 19 via the read/write section 28, and detects that the ultrasound treatment instrument 2 is connected to the power supply apparatus 3.

In next step S2, (the read circuit of) the read/write section 28 reads the final connection time Tf and the number Nc of cases of diseases which are written (recorded) in the data storage section 19b of the storage section 19 previously, and sends the final connection time Tf and the number Nc of cases of diseases to the processing section 26. The processing section 26 retains data on the final connection time Tf and the number Nc of cases of diseases in the storage section 31, a register and the like.

In next step S3, the comparison section 26b of the processing section 26 compares the number Nc of cases of diseases which is read from the ultrasound treatment instrument 2 and the second number of cases of diseases threshold value Nβ retained in the parameter data storage section 31b or the like, and determines whether or not is Nc≤Nβ satisfied.

When the condition of Nc≤Nβ is not satisfied, that is, when the number Nc of cases of diseases exceeds the second number of cases of diseases threshold value Nβ, the comparison section 26b of the processing section 26 further compares the number Nc of cases of diseases with the first number of cases of diseases threshold value Nα retained in the parameter data storage section 31b or the like and determines whether or not Nc≤Nα is satisfied in nest step S4.

When the condition of Nc≤Nα is satisfied, that is, when the number Nc of cases of diseases is equal to or smaller than the first number of cases of diseases threshold value Nα, the processing section 26 performs processing of notifying the user that the number of usable times is very small in next step S5, and the flow proceeds to processing of step S7. More specifically, as the content of which the user is notified, the processing section 26 may output the value of (Nα−Nc) to the display section 16 via the display circuit 29, and the display section 16 may display (Nα−Nc) which is the number of usable times. The user can recognize that the number of usable times is small from the value of (Nα−Nc) which is displayed or the like.

When the condition of Nc≤Nα is not satisfied in the processing of step S4, that is, when the number Nc of cases of diseases exceeds the first number of cases of diseases threshold value Nα, the processing section 26 performs processing of notifying the user that the number of usable times exceeds the number of endurable times in next step S6, and ends the processing in FIG. 5.

When the condition of Nc≤Nβ is satisfied in step S3, the non-connection time period calculation section 26c of the processing section 26 calculates Tnc=Tp−Tf as the non-connection time period Tnc which is the difference between the present time Tp and the final connection time Tf, which is obtained by the final connection time Tf being subtracted from the present time Tp from the clock section 27 in step S7. Further, in next step S8, the comparison section 26b of the processing section 26 compares the calculated non-connection time period (Tp−Tf) with the non-connection time period threshold value Tth, and determines whether or not (Tp−Tf)>Tth is satisfied, that is, whether or not the non-connection time period (Tp−Tf) reaches the non-connection time period threshold value Tth or more.

The case in which the comparison result (the determination result) by the comparison section 26b does not satisfy the condition of (Tp−Tf)>Tth, that is, the case, in which the calculated non-connection time period Tnc is equal to or smaller than the non-connection time period threshold value Tth, corresponds to the case in which the non-connection time period does not reach a time period that is required for sterilization treatment by the autoclave apparatus 5, and therefore, the case is regarded as a state in which connection is temporarily released in a state of use in one case of a disease (a state in which the ultrasound treatment instrument is connected again after temporarily detached from the power supply apparatus 3). Accordingly, in the case of the determination result, (the number of times updating section 26d of) the processing section 26 does not update the number Nc of cases of diseases, and ends the processing of FIG. 5.

A case in which the condition of (Tp−Tf)>Tth is satisfied, that is, a case of the lapse of time in which the non-connection time period Tnc exceeds the non-connection time period threshold value Tth corresponds to the case in which the non-connection time period exceeds the time period which is required for the sterilization treatment by the autoclave apparatus 5, and therefore, there is a high probability that the ultrasound treatment instrument 2 is connected to the power supply apparatus 3 after being subjected to sterilization treatment. Therefore, the parameter processing section 26g performs processing of whether or not to update the number Nc of cases of diseases based on the determination result with respect to the parameter by using the parameter set by the parameter setting section 17a. Consequently, the parameter calculation section 32 configuring the parameter processing section 26g calculates (detects) the set (selected) parameter in next step S9.

In next step S10, the comparison section 26b of the processing section 26 compares the parameter calculation value as the calculation value of the parameter which is calculated, with the corresponding parameter threshold value (Pth in FIG. 5), and determines whether or not the parameter calculation value exceeds the parameter threshold value.

In a case of the determination result that the parameter calculation value exceeds the parameter threshold value, the number of times updating section 26d of the processing section 26 updates the number Nc of cases of diseases in the storage section 19 to increase the number Nc of cases of diseases by one via the read/write section 28 in next step S11, and thereafter, ends the processing in FIG. 5.

In a case of the determination result that the calculation value of the parameter is equal to or smaller than the parameter threshold value, the flow further returns to the processing in step S9, the calculation value of the parameter at a time after the present time is calculated, and the processing in step S10 is further continued. Namely, in the processing in step S9, calculation of the parameter is performed with a lapse of time in the state in which the ultrasound treatment instrument 2 is connected to the power supply apparatus 3, and therefore, even when the calculation value of the parameter which is calculated at a certain time is equal to or smaller than the parameter threshold value, the calculation value of the parameter is also further calculated after the certain time, and processing of whether or not the calculation value of the parameter which is calculated exceeds the parameter threshold value is continued.

Subsequently, when the parameter calculation value is brought into a state of exceeding the parameter threshold value as described above, the number Nc of cases of diseases is updated to be increased by one. When the parameter calculation value is equal to or smaller than the parameter threshold value, the processing of step S9 and S10 is continued.

The present invention basically performs the processing of updating the number Nc of cases of diseases by performing the processing as shown in FIG. 5. Note that by the processing in FIG. 5, the number Nc of cases of diseases can be basically counted properly. However, in a case of such a special example of use that during use in one case of a disease, the user temporarily detaches the ultrasound treatment instrument 2 from the power supply apparatus 3, and thereafter, the user performs an operation of reconnecting the ultrasound treatment instrument 2 to the power supply apparatus 3 again, the processing of not updating the number Nc of cases of diseases is performed in the processing in FIG. 5 (because the non-connection time period Tnc (=Tp−Tf) which is calculated at the time of reconnection is shorter than the non-connection time period threshold value Tth).

In order to be able to respond suitably to the special example of use as above, in other words, in order to count the number Nc of cases of diseases more precisely, in the first embodiment of the present invention, the count flag F (as the number of times update identification information expressing the identification information of update of the number of times) is stored in the storage section 19. When the ultrasound treatment instrument 2 is shipped from a factory, the final connection time Tf, the number Nc of cases of diseases, and the count flag F are not stored in the storage section 19. After the first use, in the case in which the number Nc of cases of diseases is updated based on the determination result that the parameter calculation value exceeds the parameter threshold value as in step S11 in FIG. 5, the count flag F is updated to one (namely, the flag state expressing that the number Nc of cases of diseases is updated) and is stored in the storage section 19 with the update of the number Nc of cases of diseases.

In the case of the processing content in FIG. 5, it cannot be determined, at a time of connection (of the ultrasound treatment instrument 2 to the power supply apparatus 3) of the next time, whether the state of ending the processing in FIG. 5 is that the processing is ended after the number Nc of cases of diseases is updated as shown in step S11, or is that the processing in FIG. 5 is ended in the state in which the number Nc of cases of diseases is not updated during the operations in step S9 and S10.

In contrast with this, in a processing content shown in FIG. 6, processing of setting the count flag F to zero is performed before the operations in steps S9 and S10 in FIG. 5 are performed. By the processing being performed, it is enabled to distinguish whether the processing is ended in the state in which the number Nc of cases of diseases is not updated during the operations of steps S9 and S10, or the processing is ended after the number Nc of cases of diseases is updated as shown in step S11, based on the value (one or zero) of the count flag F at the time of the connection of the next time.

As above, in the present embodiment, the processing which can properly count the number Nc of cases of diseases is performed even in the case of the special example of use like reconnection during (use in) the case of a disease by using the determination of whether or not the count flag F is one with the determination for the non-connection time period Tnc.

FIG. 6 shows a processing procedure of the present embodiment. The user such as a surgeon connects the ultrasound treatment instrument 2 to the power supply apparatus 3, and turns on the power supply switch 15.

Thereupon, the respective sections in the power supply apparatus 3 are brought into the operation state, and in first step S20, the connection detection section 26a of the processing section 26 reads ID in the storage section 19 via the read/write section 28, and detects that the ultrasound treatment instrument 2 is connected to the power supply apparatus 3. Further, the connection detection section 26a regularly performs processing of detection of connection. For example, as will be described later, the connection detection section 26a may regularly perform processing of detection of connection simultaneously with the timing when the time updating section 26e updates the present time.

Further, in next step S21, the user sets (selects) the parameter for use in update of (evaluation of the lifespan or) the number Nc of cases of diseases from the parameter setting section 17a. The parameter may be set to a predetermined parameter set in advance at the time of factory shipment or the like on the maker side, or may be set to a parameter of default which can be changed by (the user), without being set by the user.

In next step S22, (the read circuit of) the read/write section 28 reads the final connection time Tf, the number Nc of cases of diseases and the count flag F which are written (recorded) in the data storage section 19b of the storage section 19 previously, and sends the final connection time Tf, the number Nc of cases of diseases and the count flag F to the processing section 26. The processing section 26 retains data on the final connection time Tf, the number Nc of cases of diseases and the count flag F in the storage section 31, a register and the like.

In next step S23, the comparison section 26b of the processing section 26 compares the number Nc of cases of diseases which is read from the ultrasound treatment instrument 2 with the second number of cases of diseases threshold value Nβ retained in the parameter data storage section 31b or the like, and determines whether or not Nc≤Nβ is satisfied.

When the condition of Nc≤Nβ is not satisfied, that is, when the number Nc of cases of diseases exceeds the second number of cases of diseases threshold value Nβ, the comparison section 26b of the processing section 26 further compares the number Nc of cases of diseases with the first number of cases of diseases threshold value Nα retained in the parameter data storage section 31b or the like and determines whether or not Nc≤Nβ is satisfied in next step S24.

When the condition of Nc≤Nα is satisfied, that is, when the number Nc of cases of diseases is equal to or smaller than the first number of cases of diseases threshold value Nα, the processing section 26 performs processing of notifying the user that the number of usable times is very small in next step S25, and thereafter, proceeds to processing in step S27. More specifically, as the content of which the user is notified, the processing section 26 may output the value of (Nα−Nc) to the display section 16 via the display circuit 29, and the display section 16 may display (Nα−Nc) which is the number of usable times. The user can recognize that the number of usable times is small from the value of (Nα−Nc) which is displayed or the like.

When the condition of Nc≤Nα is not satisfied in the processing of step S24, that is, when the number Nc of cases of diseases exceeds the first number of cases of diseases threshold value Nα, the processing section 26 performs processing of notifying the user that the number of usable times exceeds the number of endurable times in next step S26, and ends the processing in FIG. 6.

When the condition of Nc≤Nβ is satisfied in step S23, the non-connection time period calculation section 26c of the processing section 26 calculates the non-connection time period (Tp−Tf) which is the difference between the present time Tp and the final connection time Tf, which is obtained by the final connection time Tf being subtracted from the present time Tp from the clock section 27 in step S27. Further, in next step S28, the comparison section 26b of the processing section 26 compares the calculated non-connection time period (Tp−Tf) and the non-connection time period threshold value Tth, and determines whether or not (Tp−Tf)>Tth is satisfied.

When the comparison result (the determination result) by the comparison section 26b in step S28 does not satisfy the condition of (Tp−Tf)>Tth, that is, when the calculated non-connection time period (Tp−Tf) does not exceed the non-connection time period threshold value Tth, the flag processing section 26f of the processing section 26 determines whether or not the read count flag F is one in next step S29. In other words, the processing section 26 performs processing of whether or not to update the number Nc of cases of diseases (first processing) in accordance with the determination (identification) result of the count flag F.

When the count flag F is one, the processing section 26 determines that reconnection is performed after the state in which the number Nc of cases of diseases is properly counted, and ends the processing in FIG. 6. When the count flag F is not one, that is, when the count flag F is zero (in the state in which count for updating the number Nc of cases of diseases is not performed) or the count flag F is not written in the storage section 19 as in the state firstly used, the parameter calculation section 32 performs calculation (detection) of the set parameter in step S31. Note that in the case of the state in which the ultrasound treatment instrument 2 is firstly used, the state can be determined from the value (equivalent to zero) of the number Nc of cases of diseases.

Therefore, the case in which the count flag F is not one is highly likely to correspond to the case in which the processing of updating the number Nc of cases of diseases is ended while the parameter calculation value is in the state in which the parameter calculation value does not reach the parameter threshold value at the previous time, and therefore, the processing in step S31 is performed as described above.

Further, when the comparison result (the determination result) by the comparison section 26b satisfies the condition of Tp−Tf>Tth in step S28, that is, when the non-connection time period Tp−Tf which is calculated exceeds the non-connection time period threshold value Tth, the flag processing section 26f of the processing section 26 sets the count flag F which is read to zero, and sets the count flag F in the storage section 19 to zero by (the write circuit of) the read/write section 28 in step S30. Subsequently, after the processing of step S30, the processing section 26 proceeds to processing (second processing) in step S31. Note that the processing including the processing in step S30 which is performed by the processing section 26 may be defined as second processing.

As described above, after the count flag F is set to zero, the flow proceeds to the processing of step S31 corresponding to step S9 in FIG. 5. Subsequently, the state in which the processing is ended (connection is ended) without updating the number Nc of cases of diseases halfway through calculation (detection) of the parameter (the count flag F is zero in this case), and the state in which the number Nc of cases of diseases is updated and the processing is ended (connection is ended) (the count flag F is one in this case) can be made distinguishable at the time of the next connection.

After the parameter calculation value as the calculation value of the parameter which is set by step S31 is calculated, the comparison section 26b compares the parameter calculation value with the parameter threshold value (Pth in FIG. 6) in step S32. Subsequently, the comparison section 26b determines whether or not the parameter calculation value exceeds the parameter threshold value.

In a case of the determination result that the parameter calculation value exceeds the parameter threshold value, the number of times updating section 26d of the processing section 26 increases the number Nc of cases of diseases in the storage section 19 by one via the read/write section 28, and updates the count flag F to one in next step S33, and thereafter, ends the processing in FIG. 6.

In a case of the determination result that the calculation value of the parameter in step S32 is equal to or smaller than the parameter threshold value, the flow returns to the processing in step S31, the calculation value of the parameter at a time after the present determination result, and the processing in step S32 is further continued.

Namely, in the processing in step S31, calculation of the parameter is performed with a lapse of time in the state in which the ultrasound treatment instrument 2 is connected to the power supply apparatus 3, and therefore, even when the calculation value of the parameter which is calculated at a certain time does not exceed the parameter threshold value, the calculation value of the parameter is also calculated after the certain time, and processing of whether or not the calculation value of the parameter which is calculated is in a state of exceeding the parameter threshold value is continued.

Subsequently, when the parameter calculation value is brought into the state of exceeding the parameter threshold value as described above, the number Nc of cases of diseases is increased by one, and the count flag F is updated to one. In contrast with this, when the parameter calculation value is equal to or smaller than the parameter threshold value, the processing in steps S31 and S32 is continued.

By the processing shown in FIG. 6 being performed, the number Nc of cases of diseases can be counted precisely. In other words, the surgical system 1 which can detect the lifespan of the ultrasound treatment instrument more precisely by enabling presence or absence of sterilization treatment to be determined more precisely can be provided. Specific examples of the processing of steps S9 and S10 in FIG. 5, or the processing of steps S31 and S32 in FIG. 6 are as shown in FIG. 7A to FIG. 7G. Note that FIG. 7A shows the case in which the set parameter is the number of output times with the case of performing the processing shown in FIG. 5, for example, but FIG. 7A can be similarly applied to the case of the processing in FIG. 6.

The processing of steps S1 to S8 in FIG. 7A is the same as in FIG. 5. When the condition of (Tp−Tf)>Tth is not satisfied in step S8, the processing section 26 ends the processing in FIG. 7A.

When the condition of (Tp−Tf)>Tth is satisfied, the number of output times calculation section 33 determines presence or absence of turning on the switch to output (to the ultrasound transducer 11 from the output section 23) by an ON/OFF operation of the foot switch 13 from the detection signal by the switch detection section 41, for example in step S41a. In this case, for example, the number of output times calculation section 33 determines whether the switch is turned on to output.

When the foot switch 13 is not turned on from off, the processing of step S41a is continued, and when the foot switch is turned on to output, in next step S41b, the number of output times calculation section 33 performs processing of counting the number of output times so as to increase the number of output times by one, and thereafter, outputs the count value of the number of output times to the comparison section 26b. Note that an initial value of the count of the number of output times is set to zero.

In next step S41c, the comparison section 26b compares the count value of the number of output times with ten times which is the number of output times threshold value. In a case of a comparison result (a determination result) that the count value of the number of output times exceeds ten times in step S41c, the number of times updating section 26d performs processing of increasing the number Nc of cases of diseases by one in step S11.

In a case of a comparison result (a determination result) that the count value of the number of output times does not exceed ten times, the flow returns to the processing of step S41a. By the processing in FIG. 7A, the number Nc of cases of diseases to be a criterion for the lifespan of the ultrasound treatment instrument 2 can be precisely counted using the number of output times as a parameter. Accordingly, the surgical system 1 which can detect the lifespan of the ultrasound treatment instrument 2 more precisely can be provided.

In FIG. 7B to FIG. 7G that will be described as follows, similar processing is practically performed with parameters only differing from the parameter in FIG. 7A. Similar operational effects are provided except that the parameters are different.

FIG. 7B shows processing in a case in which the set parameter is the output time period, more specifically, a continuous output time period in a case of output being made continuously. Note that in FIG. 7B, a case of a processing content that does not perform steps S3 to S6 in FIG. 7A, for example, is described, but the processing also can be applied to a case of a processing content that performs steps S3 to S6 similarly to the case of FIG. 7A, and also can be applied to the case of using the count flag F as shown in FIG. 6.

Steps S1 and S2 in FIG. 7B are similar to steps S1 and S2 in FIG. 5. After the processing of step S2, the flow goes to step S7, and after step S7, processing of step S8 is performed. Processing of steps S7 and S8 in FIG. 7B is similar to the processing in steps S7 and S8 in FIG. 5, and when the condition of (Tp−Tf)>Tth is not satisfied in step S8, the processing section 26 ends the processing in FIG. 7B.

When the condition of (Tp−Tf)>Tth is satisfied, the continuous output time period calculation section 34a of the output time period calculation section 34 determines presence or absence of turning on the foot switch to output (to the ultrasound transducer 11 from the output section 23) by an ON/OFF operation on the foot switch 13 from the detection signal by the switch detection section 41, for example, in step S42a. In this case, the continuous output time period calculation section 34a determines whether the foot switch is turned on to output.

When the foot switch 13 is not switched on from off, the continuous output time period calculation section 34a returns the count value of the output time period to the initial value of zero in step S42a, and thereafter, returns to the processing of step S42a. When the foot switch is turned on to output, in step S42c, the continuous output time period calculation section 34a performs processing of counting the output time period from the initial value by using the present time of the clock section 27, and thereafter outputs the count value of the output time period to the comparison section 26b.

In next step S42d, the comparison section 26b compares (the count value of) the output time period with three seconds which is the continuous output time period threshold value. In step S42d, in a case of a comparison result (a determination result) that the output time period exceeds three seconds, the number of times updating section 26d performs processing of increasing the number Nc of cases of diseases by one in step S11. In a case of a comparison result (a determination result) that the output time period does not exceed three seconds, the flow returns to the processing in step S42b. FIG. 7B has an operational effect substantially similar to the operational effect in FIG. 7A except that the kind of the parameter differs.

FIG. 7C shows processing in a case in which the set parameter is the integrated value of the output time period.

Processing of steps S1, S2, S7 and S8 in FIG. 7C is the same as in FIG. 7B. In step S8, when the condition of (Tp−Tf)>Tth is not satisfied; the processing section 26 ends the processing in FIG. 7C.

When the condition of (Tp−Tf)>Tth is satisfied, in step S43a, the output time period integrated value calculation section 34b of the output time period calculation section 34 determines presence or absence of turning on the foot switch to output (to the ultrasound transducer 11 from the output section 23) by an ON/OFF operation on the foot switch 13 from the detection signal by the switch detection section 41, for example. In this case, the output time period integrated value calculation section 34b determines whether the foot switch is turned on to output.

When the foot switch 13 is not turned on from off, the flow returns to the processing in step S43a. When the foot switch is turned on to output, in step S43b, the output time period integrated value calculation section 34b performs processing of integrating the output time period by using the present time of the clock section 27, and thereafter, outputs the integrated output time period to the comparison section 26b.

In next step S43c, the comparison section 26b compares the integrated output time period (that is, the output time period integrated value) with one minute that is the output time period integration threshold value. In a case of a comparison result (a determination result) that the output time period integrated value exceeds one minute in step S43c, the number of times updating section 26d performs processing of increasing the number Nc of cases of diseases by one in step S11.

In a case of a comparison result (a determination result) that the output time period does not exceed one minute, the flow returns to the processing in step S43a. FIG. 7C has an operational effect similar to that in FIG. 7B except that the kind of the parameter differs.

FIG. 7D shows processing in a case of the integrated value of the output current as the set parameter.

Processing of steps S1, S2, S7 and S8 in FIG. 7D is the same as the processing in FIG. 7B. In step S8, when the condition of (Tp−Tf)>Tth is not satisfied, the processing section 26 ends the processing in FIG. 7D.

When the condition of (Tp−Tf)>Tth is satisfied, the output current integrated value calculation section 36 determines presence or absence of turning on the foot switch to output (to the ultrasound transducer 11 from the output section 23) by the ON/OFF operation on the foot switch 13 from the detection signal by the switch detection section 41, for example in step S44a. In this case, the output current integrated value calculation section 36 determines whether the foot switch is turned on to output.

When the foot switch 13 is not turned on from off, the flow returns to the processing of step S44a. When the foot switch is turned on to output, the output current integrated value calculation section 36 integrates the drive current detected by the current detection circuit 25b as the output current in step S44b. The output current integrated value calculation section 36 outputs the integrated output current to the comparison section 26b.

In next step S44c, the comparison section 26b compares the integrated output current (namely, the output current integrated value) with 0.5 A·s which is the output current integration threshold value. In step S44c, in a case of a comparison result (a determination result) that the output current integrated value exceeds 0.5 A·s, the number of times updating section 26d performs processing of increasing the number Nc of cases of diseases by one in step S11. In a case of a comparison result (a determination result) that the output current integrated value does not exceed 0.5 A·s, the flow returns to the processing of step S44a. FIG. 7D has a similar operational effect to that in FIG. 7B except that the kind of the parameter differs.

FIG. 7E shows processing in a case of the integrated value of the output voltage as the set parameter.

Processing of steps S1, S2, S7 and S8 in FIG. 7E is the same as that in FIG. 7B. When the condition of (Tp−Tf)>Tth is not satisfied in step S8, the processing section 26 ends the processing in FIG. 7E.

When the condition of (Tp−Tf)>Tth is satisfied, the output voltage integrated value calculation section 37 determines presence or absence of turning on the foot switch to output (to the ultrasound transducer 11 from the output section 23) by an ON/OFF operation on the foot switch 13 from the detection signal by the switch detection section 41, for example, in step S45a. In this case, the output voltage integrated value calculation section 37 determines whether the foot switch is turned on to output.

When the foot switch 13 is not turned on from off, the flow returns to the processing of step S45a. When the foot switch is turned on to output, the output power integrated value calculation section 37 integrates the drive voltage detected by the voltage detection circuit 25a as the output voltage in step S45b. The output voltage integrated value calculation section 37 outputs the integrated output voltage to the comparison section 26b.

In next step S45c, the comparison section 26b compares the integrated output voltage (namely, the output voltage integrated value) with 600 V·s which is the output voltage integration threshold value. In step S45c, in a case of a comparison result (a determination result) that the output voltage integrated value exceeds 600 V·s, the number of times updating section 26d performs processing of increasing the number Nc of cases of diseases by one in step S11. In a case of a comparison result (a determination result) that the output voltage integrated value does not exceed 600 V·s, the flow returns to the processing in step S45a. FIG. 7E has an operational effect similar to that in FIG. 7B except that the kind of the parameter differs.

FIG. 7F shows processing in a case of the integrated value of the output power as the set parameter.

Processing of steps S1, S2, S7 and S8 in FIG. 7F is the same as that in FIG. 7B. When the condition of (Tp−Tf)>Tth is not satisfied in step S8, the processing section 26 ends the processing in FIG. 7F.

When the condition of (Tp−Tf)>Tth is satisfied, for example, the output voltage integrated value calculation section 35b as the output energy calculation section, determines presence or absence of turning on the foot switch to output (to the ultrasound transducer 11 from the output section 23) by an ON/OFF operation on the foot switch 13 from the detection signal by the switch detection section 41, for example, in step S46a. In this case, the output power integrated value calculation section 35b determines whether the foot switch is turned on to output.

When the foot switch 13 is not turned on from off, the flow returns to the processing of step S46a. When the foot switch is turned on to output; the output power integrated value calculation section 35b integrates the output power that is a product of the drive voltage and the output current which are respectively detected by the voltage detection circuit 25a and the current detection circuit 25b. The output power integrated value calculation section 35b outputs the integrated output power to the comparison section 26b.

In next step S46c, the comparison section 26b compares the integrated output power (namely, the output power integrated value) with 100 W·s which is the output power integration threshold value. In step S46c, in a case of a comparison result (a determination result) that the output power integrated value exceeds 100 W·s, the number of times updating section 26d performs processing of increasing the number Nc of cases of diseases by one in step S11. In a case of a comparison result (a determination result) that the output power integrated value does not exceed 100 W·s, the flow returns to the processing of step S46a. FIG. 7F has an operational effect similar to that in FIG. 7B except that the kind of the parameter differs.

FIG. 7G shows processing in a case of the connection time period as the set parameter. The connection time period means a time period in which the ultrasound treatment instrument 2 is continuously (continually) connected to the power supply apparatus 3.

Processing of steps S1, S2, S7 and S8 in FIG. 7G is the same as that in FIG. 7B. When the condition of (Tp−Tf)>Tth is not satisfied in step S8, the processing section 26 ends the processing in FIG. 7G.

When the condition of (Tp−Tf)>Tth is satisfied, in step S47a, the connection time period calculation section 38 calculates the connection time period in which the ultrasound treatment instrument 2 is continuously connected by using the present time of the clock section 27 from the time at which the ultrasound treatment instrument 2 is connected to the power supply apparatus 3, and outputs the calculated connection time period to the comparison section 26b.

In next step S47b, the comparison section 26b compares the calculated connection time period with 10 minutes which is the connection time period threshold value. In step S47c, in a case of a comparison result (a determination result) that the connection time period exceeds 10 minutes, the number of times updating section 26d performs processing of increasing the number Nc of cases of diseases by one in step S11.

In a case of a comparison result (a determination result) that the connection time period does not exceed one minute, the flow returns to the processing in step S47a. FIG. 7G has an operational effect similar to that in FIG. 7B except that the kind of the parameter differs.

Further, FIG. 7H shows a processing content of a modification of FIG. 7G. FIG. 7H shows the processing content which, in FIG. 7G, updates the number Nc of cases of diseases, or does not update the number Nc of cases of diseases, and ends the processing, based on whether or not the non-connection time period Tnc exceeds the non-connection time period threshold value Tth as the predetermined time period, or 60 minutes as one specific example of the predetermined time period.

More specifically, processing of steps S1, S2 and S7 in FIG. 7H is the same as that in FIG. 7B and FIG. 7G. The non-connection time period (Tp–Tf) which is calculated in step S7 is sent to the comparison section 26b, and in next step S48, the comparison section 26b performs comparison of whether or not the non-connection time period (Tp–Tf) exceeds 60 minutes. Namely, the comparison section 26b performs determination of whether or not the condition of (Tp–Tf)>60 minutes is satisfied. In a case of a comparison result (a determination result) that the condition of (Tp–Tf) >60 minutes is satisfied, the number of times updating section 26d performs processing of increasing the number Nc of cases of diseases by one in next step. S11. In a case of a comparison result (a determination result) that the non-connection time period (Tp–Tf) does not exceed 10 minutes, the processing in FIG. 7H is ended.

According to the present modification, by the simple processing using the calculation result of the non-connection time period (Tp–Tf), whether to update or not to update the number Nc of cases of diseases can be performed. According to the present modification, the number Nc of cases of diseases can be counted while predetermined precision is ensured, by the simple processing.

Figure 8A:
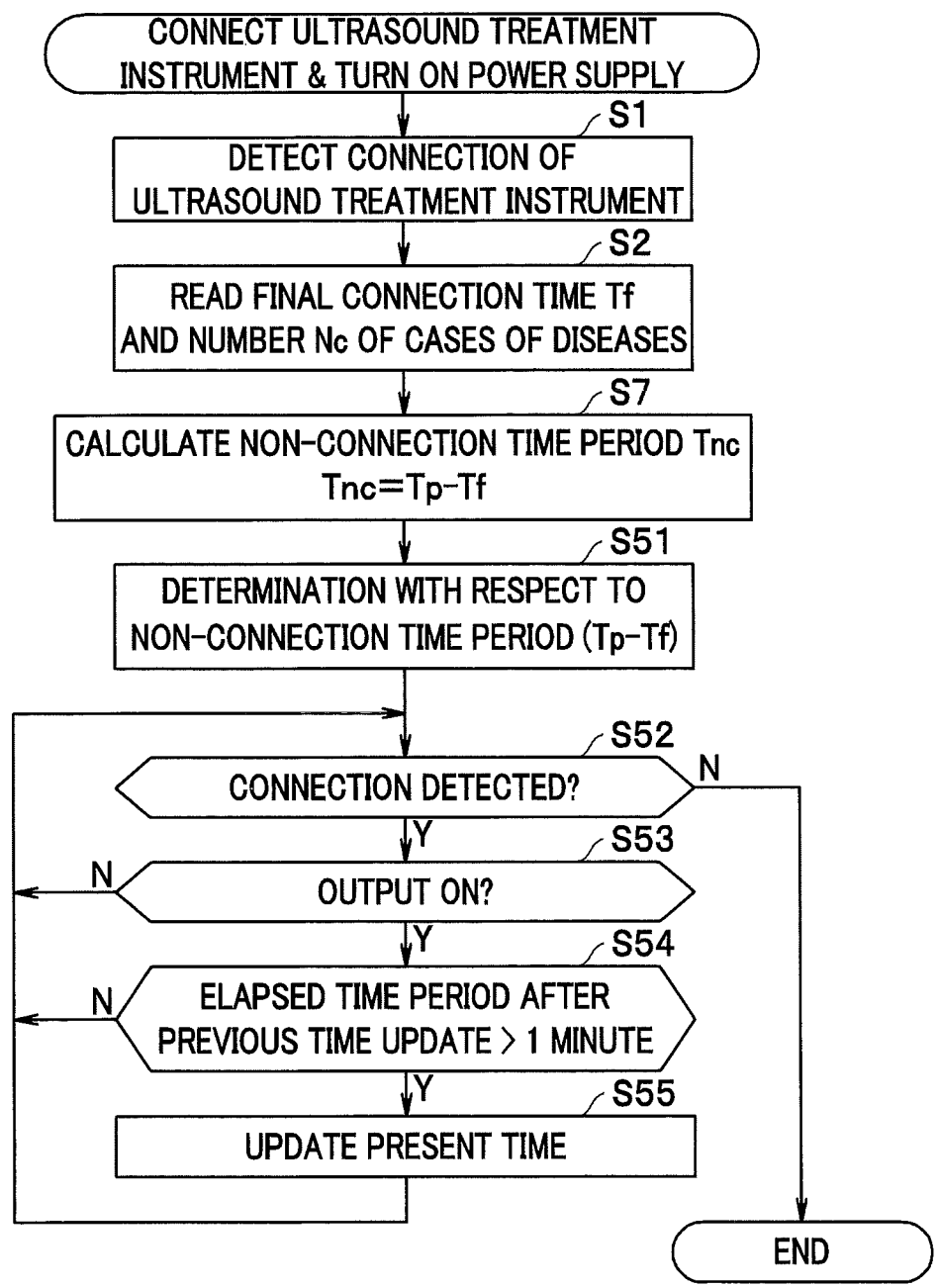
FIG. 8A is a flowchart showing a processing content of updating a present time which is stored in an ultrasound treatment instrument by a time updating section.

Further, in the aforementioned first embodiment except for FIG. 7H, the present time which is stored in the storage section 19 is regularly updated by the time updating section 26e in the case of the connection state in which the ultrasound treatment instrument 2 is connected to the power supply apparatus 3. FIG. 8A shows a processing example of updating the time.

Steps S1 and S2 in FIG. 8A are the same processing as the processing of steps S1 and S2 in FIG. 5, for example. Describing simply, a user such as a surgeon connects the ultrasound treatment instrument 2 to the power supply apparatus 3, and turns on the power supply switch 15. Thereupon, the respective sections in the power supply apparatus 3 are in the operation state, and in first step S1, the connection detection section 26a reads ID in the storage section 19 and detects that the ultrasound treatment instrument 2 is connected to the power supply apparatus 3.

In next step S2, the read/write section 28 reads the final connection time Tf and the number Nc of cases of diseases which are written (recorded) previously in the data storage section 19b of the storage section 19, and further, the processing section 26 retains the data on the final connection time Tf and the number Nc of cases of diseases in the storage section 31 or the like.

Further, in FIG. 8A, after step S2, processing of calculating the non-connection time period Tnc of step S7 is performed. After the processing of step S7, the determination processing with respect to the non-connection time period Tnc is performed in step S51. Note that the processing in step S51 is the same processing as the processing of step S8 in FIG. 5, for example; but the time updating section 26e performs the following processing irrespective of the determination result with respect to the non-connection time period Tnc.

After the processing of step S51, the time updating section 26e determines (detects) whether it is a connection detection state in which the ultrasound treatment instrument 3 is connected to the power supply apparatus 3 by using the detection result by the connection detection section 26a via the connection detection section 26a in next step S52. Note that in this case, it may be also determined (detected) simultaneously that the power supply apparatus 3 is turned on. When the time updating section 26e operates only in the state in which the power supply apparatus 3 is turned on, it does not have to be detected that the power supply apparatus 3 is turned on.

When the ultrasound treatment instrument 3 is not connected to the power supply apparatus 3 in step S52, the processing in FIG. 8A is ended. When the ultrasound treatment instrument 3 is connected to the power supply apparatus 3, in next step S53 the time updating section 26e determines presence or absence of output, for example, whether the switch is turned on to output. The determination processing is the same processing as that of step S41a mentioned above or the like. When the switch is turned on to output, the flow returns to the processing of step S52, and when the switch is turned off to stop output, the time updating section 26e determines whether or not a fixed time, for example, one minute or more elapses after the update of the time of the previous time in next step S54.

When one minute or more does not elapse in step S54, the flow returns to the processing of step S52, and when one minute or more does not elapse contrary to the above, the flow proceeds to processing of step S55. In step S55, the time updating section 26e updates the present time (which is old) before the update in the storage section 19 to the present time Tp, and thereafter, returns to the processing in step S52.

As above, the times updating section 26d updates the present time in the storage section 19 at substantially fixed time intervals. Note that in FIG. 8A, processing of proceeding to the processing of step S55 from step S53 without performing step S54 may be performed. In this case, the processing is as in FIG. 8B.

Figure 8B:
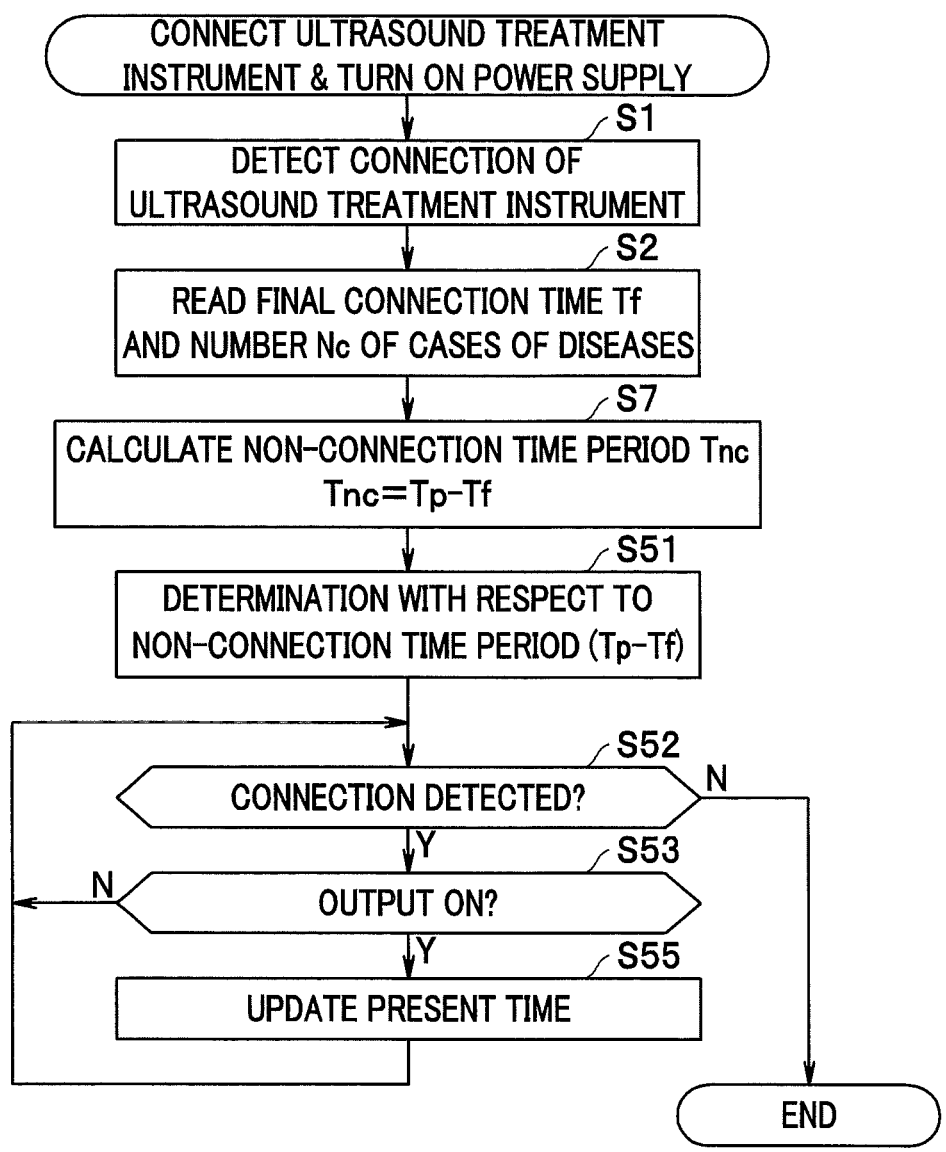

In a case of FIG. 8B, in the time period in which the ultrasound output is not performed, the present time is updated at time intervals which is substantially close to continuously.

As shown in FIG. 8A or FIG. 8B, the time updating section 26e substantially regularly updates the present time which is retained (stored) in the storage section 19. Therefore, during the processing of steps S9 and S10 in FIG. 5, and steps S31 and 32 in FIG. 6, the present time in the storage section 19 is updated substantially regularly. However, update of the present time in this case does not influence determination of whether or not the parameter calculation value exceeds the parameter threshold value.

Figure 9:
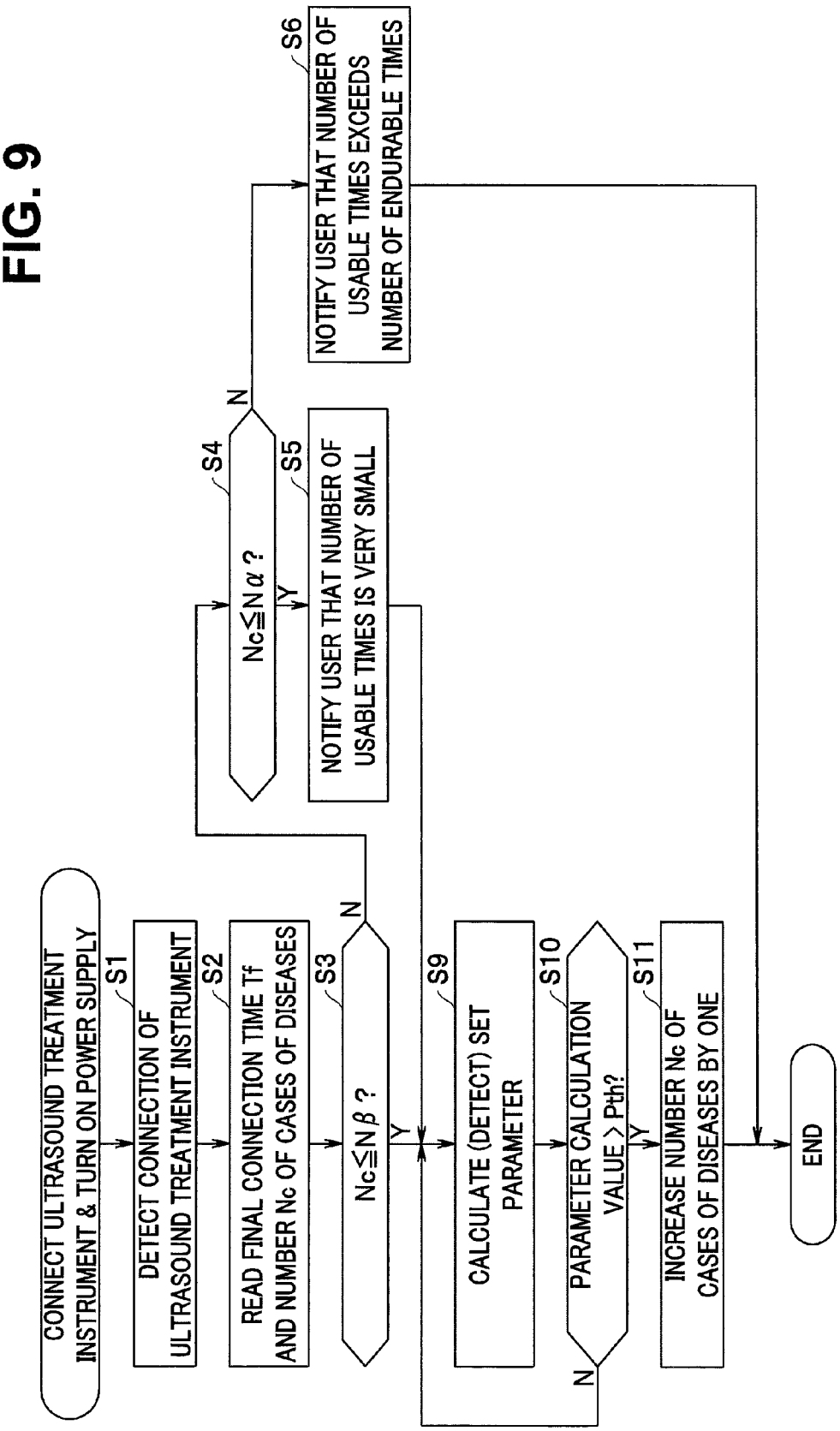
FIG. 9 is a flowchart showing a processing content of notifying a user of a number of use times by omitting part of the processing in FIG. 5.

Further, in FIG. 5, FIG. 6 and the like described above, the content that notifies the user of the determination result of the number Nc of cases of diseases is described, but as shown in FIG. 9, for example, the content may be changed to a processing content which differs from that in FIG. 5. In FIG. 9, the processing content is changed to a processing content which does not perform the processing of steps S7 and S8 in FIG. 5. In FIG. 9, the flow proceeds to the processing of step S9 when the condition of Nc≤Nβ is satisfied in step S3. Like this, FIG. 9 shows the processing content that notifies user of the determination result of the number Nc of cases of diseases irrespective of the non-connection time period Tnc.

Figure 10:
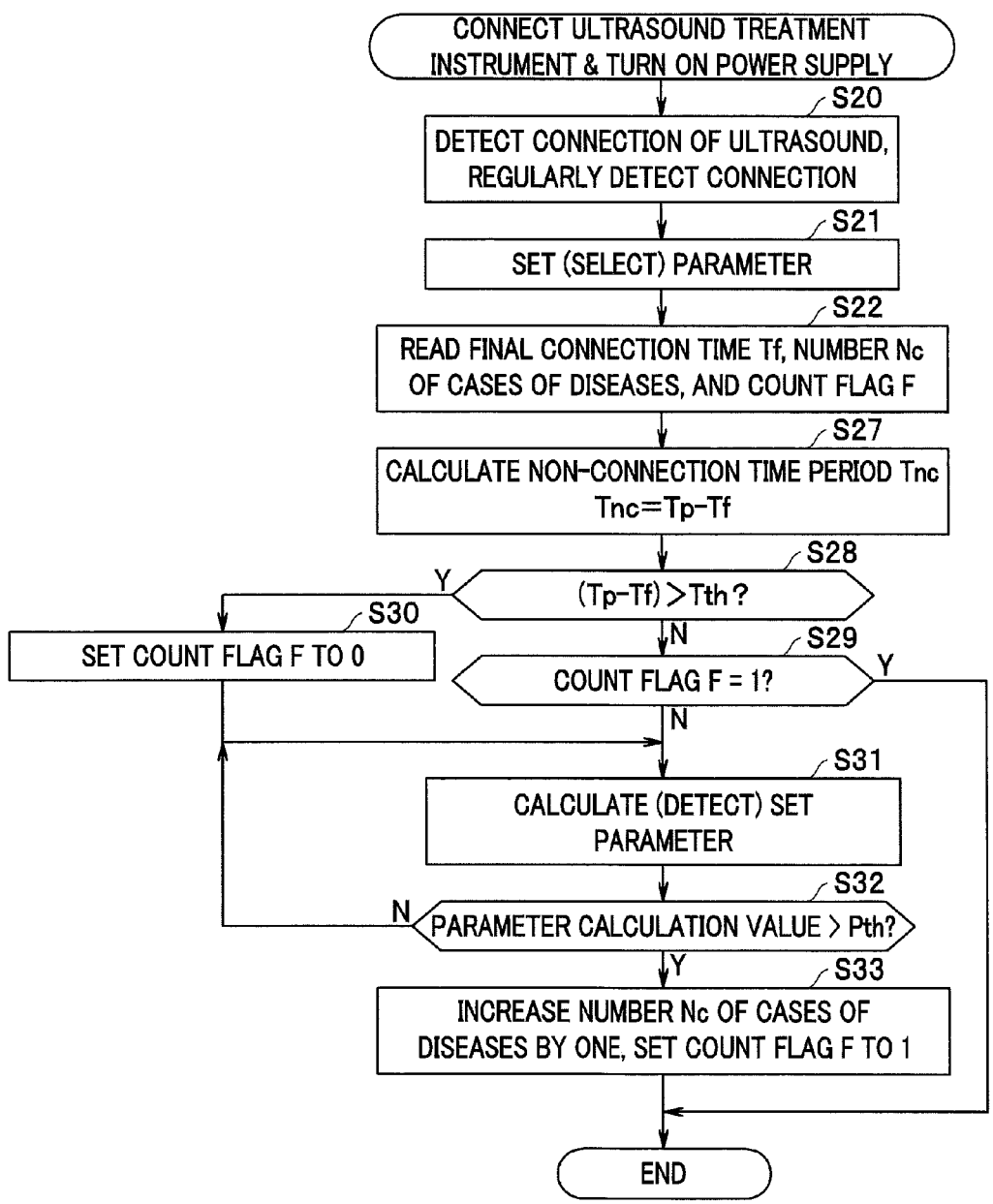
FIG. 10 is a flowchart showing a processing content in a modification of FIG. 6.

Further, as shown in FIG. 10, the determination processing with respect to the number Nc of cases of diseases, and the processing of notifying the user of the determination result of the number Nc of cases of diseases are omitted in FIG. 6, for example, and the processing with respect to the non-connection time period Tnc may be performed. More specifically, FIG. 10 shows a processing content in which the processing of steps S23 to S26 is not performed in FIG. 6. More specifically, in FIG. 10, after the processing of step S22, the flow proceeds to the processing of step S27. Except for this, the processing similar to the processing in FIG. 6 is performed.

Figure 11:
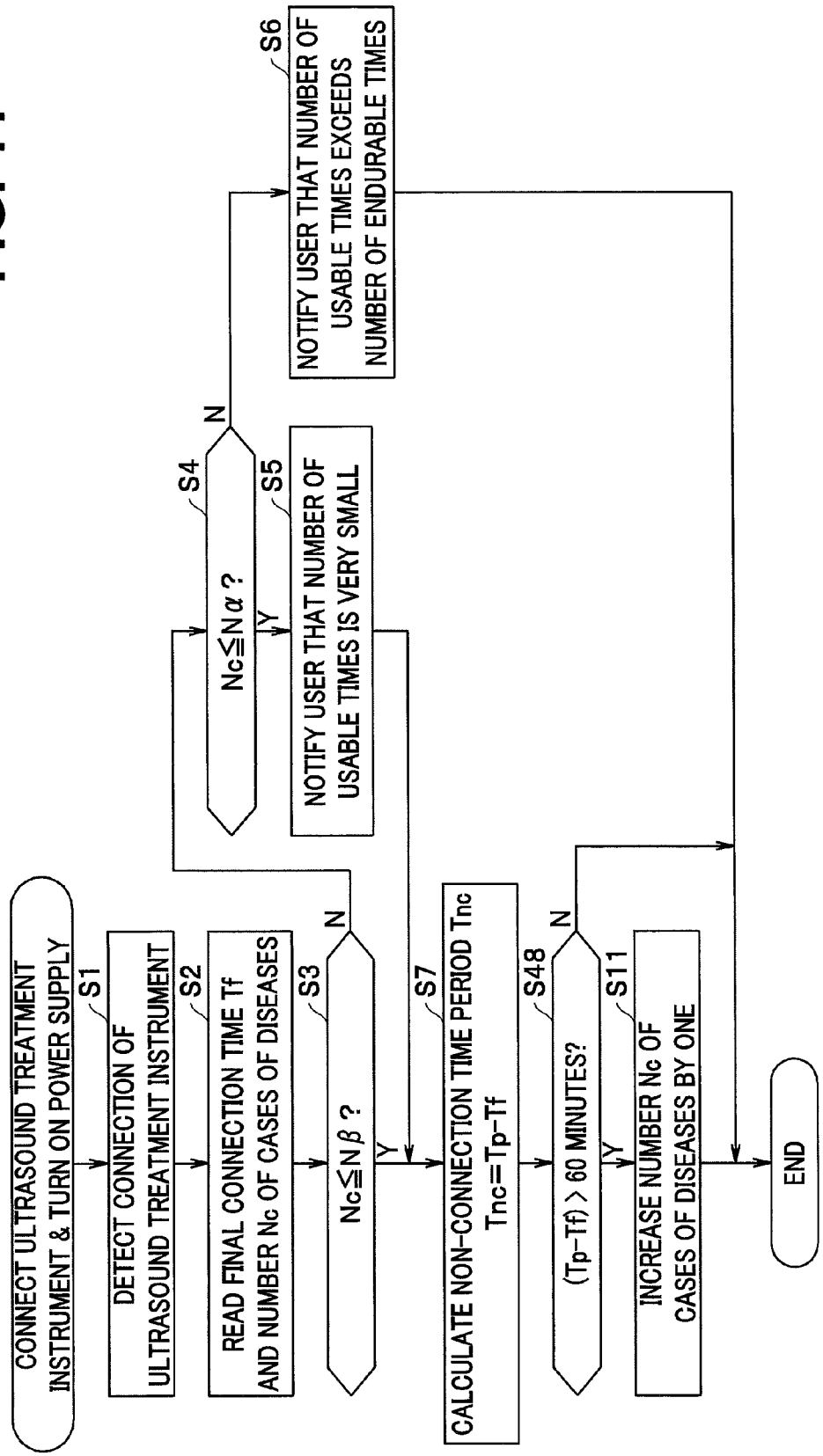
FIG. 11 is a flowchart showing a processing content in a modification of FIG. 7H.

Further, FIG. 11 shows a processing content in the case of the modification in FIG. 7H. In FIG. 7H, the processing shown in FIG. 5 (steps S3 to S6) may be additionally performed. In FIG. 11, the determination processing with respect to the number Nc of cases of diseases, and the processing of notifying the user of the determination result of the number Nc of cases of diseases are performed in the processing in FIG. 7H.

Figure 12:
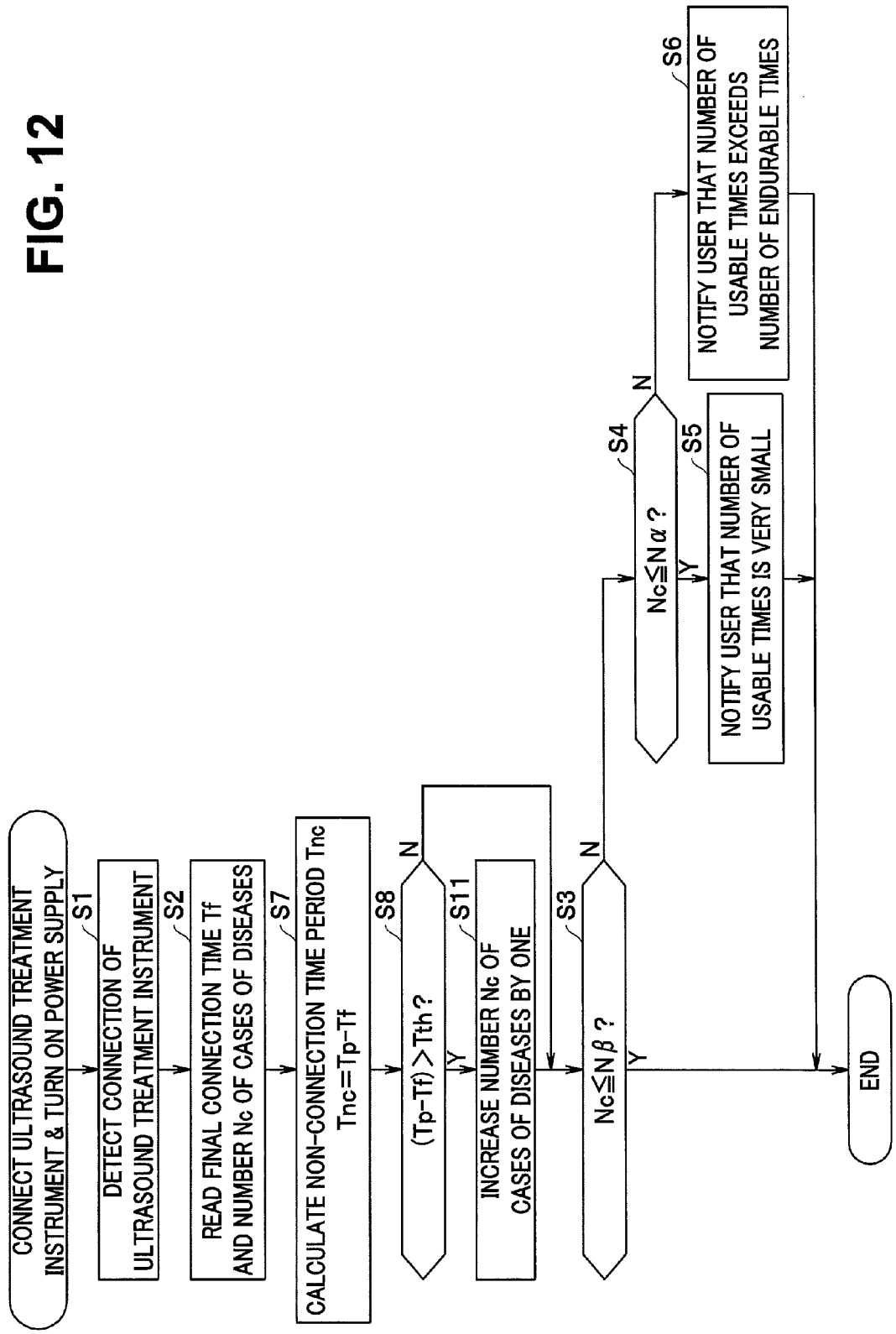
FIG. 12 is a flowchart showing a processing content in which part of the processing in FIG. 5 is deleted, and a sequence of processing is further changed.

Further, as shown in FIG. 12, a sequence of part of the processing may be changed in the processing shown in FIG. 5. Note that in FIG. 12, a processing content in which the processing of the parameter (S9 and S10) in FIG. 5 is omitted is shown.

In FIG. 12, after the processing of step S2, the flow proceeds to processing of step S7 without step S3 in FIG. 5 being performed. After the processing of step S7, processing of step S8 is performed, and when the calculated non-connection time period (Tp−Tf) exceeds the non-connection time period threshold value Tth, the number Nc of cases of diseases is updated as shown in step S11, after which, the flow proceeds to the processing of step S3.

When the non-connection time period (Tp−Tf) does not exceed the non-connection time period threshold value Tth, the flow proceeds to the processing of step S3 without performing the processing of step S11. In step S3, it is determined whether or not Nc≤Nβ is satisfied, and in a case of Nc≤Nβ, the processing in FIG. 12 is ended, whereas in a case of Nc>Nβ, it is determined whether or not Nc≤Nα is satisfied in step S4.

In a case of Nc≤Nα, the user is notified that the number of usable times is very small in step S5, and the processing in FIG. 12 is ended. In a case of Nc>Nα, the user is notified that the number of usable times exceeds the number of endurable times in step S6, and the processing in FIG. 12 is ended.

As compared with the case of the processing in FIG. 5, the processing in FIG. 12 is substantially similar processing except that the processing of notifying the user in steps S5 and S6 can differ by approximately one time when the number Nc of cases of diseases is a value close to Nα and Nβ.

Note that the processing in FIG. 12 differs from the processing in FIG. 5 in that in FIG. 5, calculation of the parameter, and the determination with respect to the calculated value are performed in steps S9 and S10, whereas in FIG. 12, the processing of steps S9 and S10 is not performed. In FIG. 12, the processing of steps S9 and S10 may be performed.

Further, the information on the shipping date and time Tm is stored in the storage section 19 of the ultrasound treatment instrument 2, the information on the shipping date and time Tm is read when the ultrasound treatment instrument 2 is connected to the power supply apparatus 3, and the use time period and the like of the ultrasound treatment instrument 2 may be limited in accordance with the elapsed days and time period Tc up to the present time Tp from the shipping date and time Tm.

Figure 13:
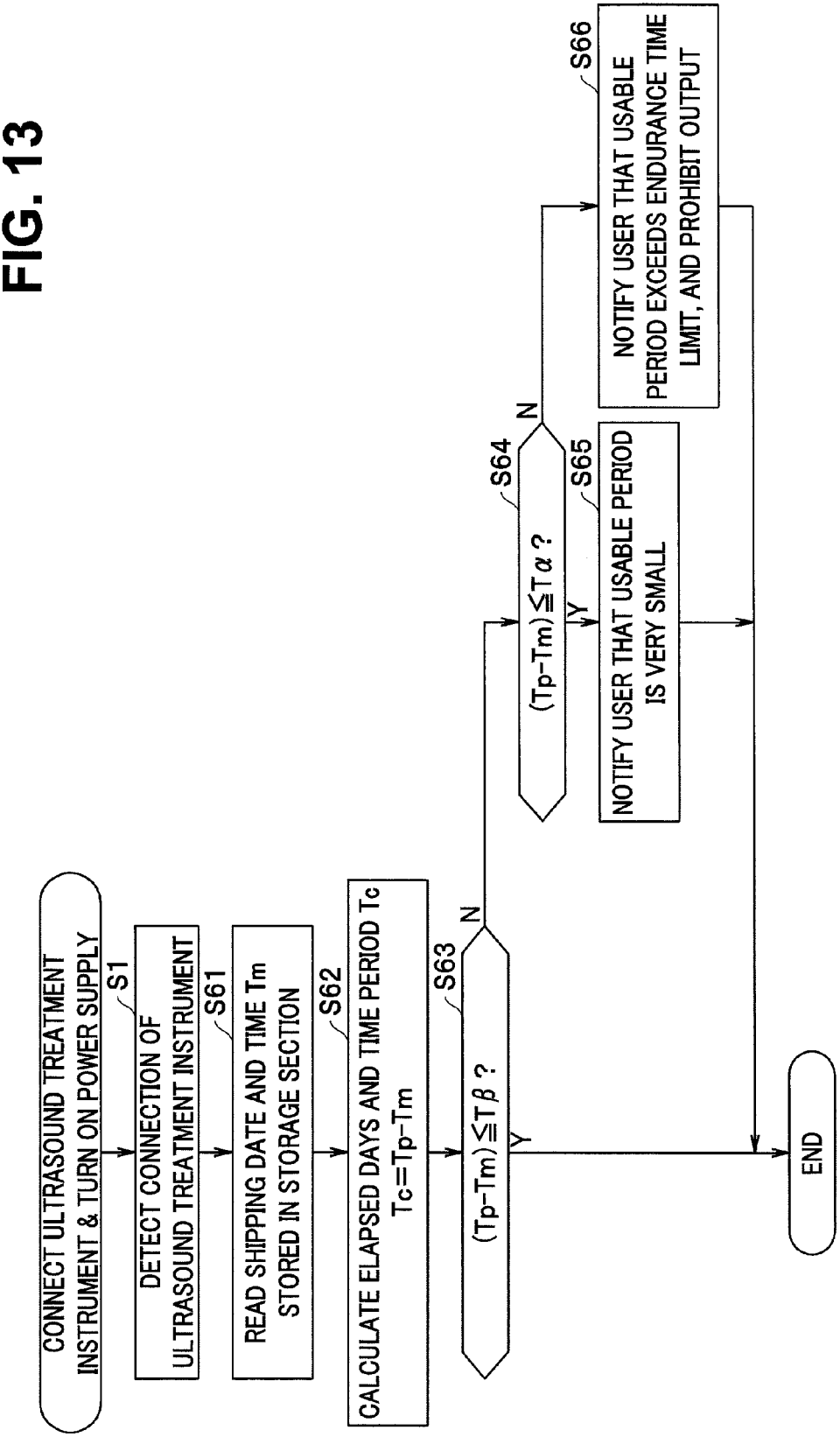
FIG. 13 is a flowchart showing a processing content of determining a lifespan by using information of a shipping date and time of the ultrasound treatment instrument.

FIG. 13 shows a processing content that limits the use time period and the like of the ultrasound treatment instrument 2 in accordance with the elapsed days and time period Tc.

After step S1 shown in FIG. 13, the read/write section reads the information on the shipping date and time Tm from the storage section 19 of the ultrasound treatment instrument 2 in step S61, and further, in step S62, the elapsed days and time period calculation section configured by the non-connection time period calculation section 26c calculates the elapsed days and time period Tc up to the present time Tp by using the shipping date and time Tm. Namely, the elapsed days and time calculation section calculates the elapsed days and time period Tc by Tc=Tp−Tm, and outputs the elapsed days and time period Tc to the comparison section 26b.

In next step S63, the comparison section 26b compares (determines) whether or not the calculated elapsed days and time period (Tp−Tm) is smaller than the elapsed days and time period threshold value Tβ which is on a verge or the like of the elapsed days and time period threshold value (or an endurance time limit) Tα corresponding to the lifespan. The elapsed days and time period threshold value Tβ is set to a value smaller by at least one day than the elapsed days and time period threshold value (or the endurance time limit) Tα, for example.

In a case of (Tp−Tm)<Tβ, the processing in FIG. 13 is ended, and when (Tp−Tm)<Tβ is not satisfied conversely, that is, in a case of (Tp−Tm)≥Tβ, the comparison section 26b compares (determines) whether or not the calculated elapsed days and time period (Tp−Tm) is smaller than the elapsed days and time period threshold value Tα corresponding to the lifespan in step S64. In a case of (Tp−Tm)<Tα, the processing section 26 performs processing of notifying the user that the usable time period is very small in step S65, and ends the processing in FIG. 13. More specifically, the processing section 26 outputs a value of Tα−(Tp−Tm) to the display section 16 via the display circuit 29, and displays Tα−(Tp−Tm) which is the usable time period on the display section 16.

When the condition of (Tp−Tm)≤Tα is not satisfied in the processing of step S64, namely, when the elapsed days and time period (Tp−Tm) exceeds the elapsed days and time period threshold value Tα corresponding to the lifespan, in next step S66, the processing section 26 performs processing of notifying the user that the usable period exceeds the endurance time limit, and performs the processing of prohibiting a drive output to the ultrasound treatment instrument 2, and ends the processing in FIG. 13.

By the processing as in FIG. 13 being performed, use exceeding the endurance time limit can be effectively prevented. Further, when a date and time immediately before the endurance time limit arrives, the user can be notified that the endurance time limit is near.

Figure 14:
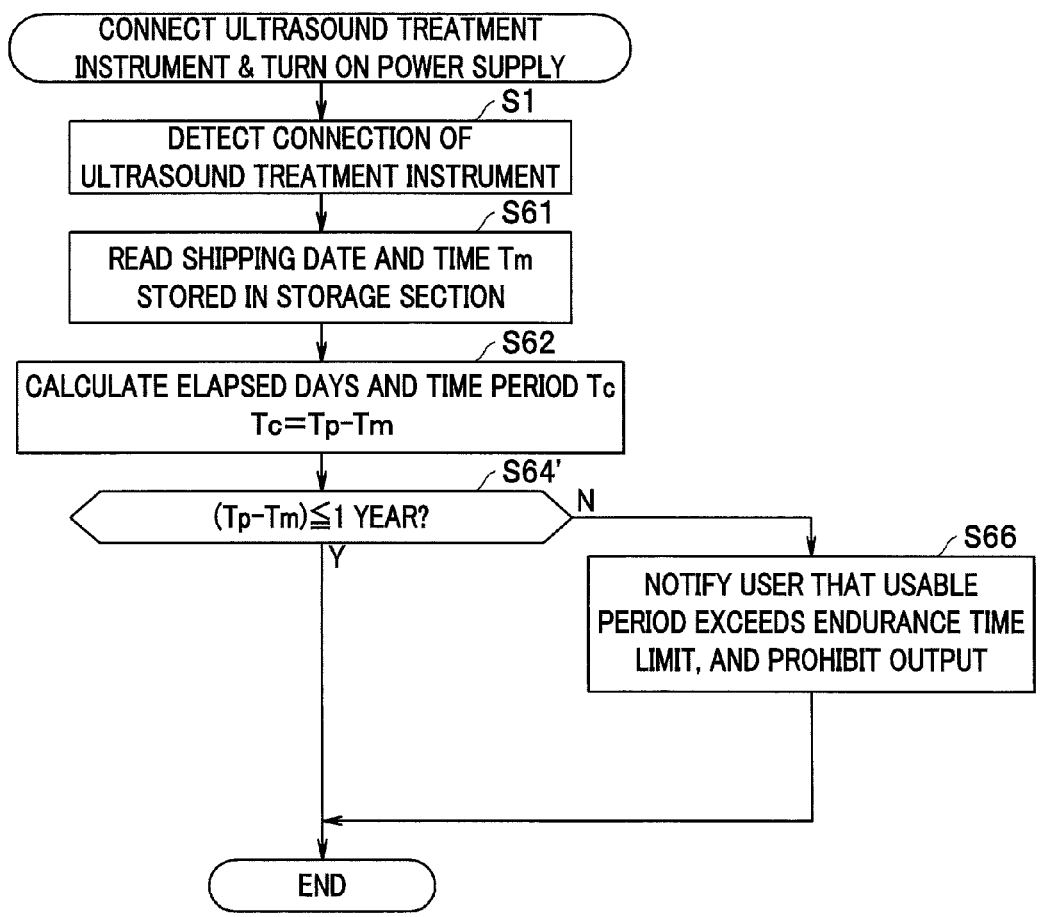
FIG. 14 is a flowchart showing a processing content partially different from FIG. 13.

Further, as a modification of FIG. 13, processing shown in FIG. 14 may be performed with use of one year as an elapsed days and time period threshold value corresponding to the endurance time limit.

In FIG. 14, same processing as the processing in FIG. 14 is performed in steps S1, S61 and S62. After the processing of step S62, in step S64' corresponding to step S64 in FIG. 13, the comparison section 26b determines whether or not the calculated elapsed days and time period (Tp−Tm) is within one year corresponding to the lifespan.

When the elapsed days and time period (Tp−Tm) does not exceed one year, the processing in FIG. 14 is ended. When the elapsed days and time period (Tp−Tm) exceeds one year, the processing section 26 performs processing of notifying the user that the usable period exceeds the endurance time limit, performs processing of prohibiting the drive output to the ultrasound treatment instrument 2 in step S66, and ends the processing in FIG. 14.

According to the configuration which performs the processing content in FIG. 14, use exceeding the endurance time limit can be effectively prevented.

Figure 15:
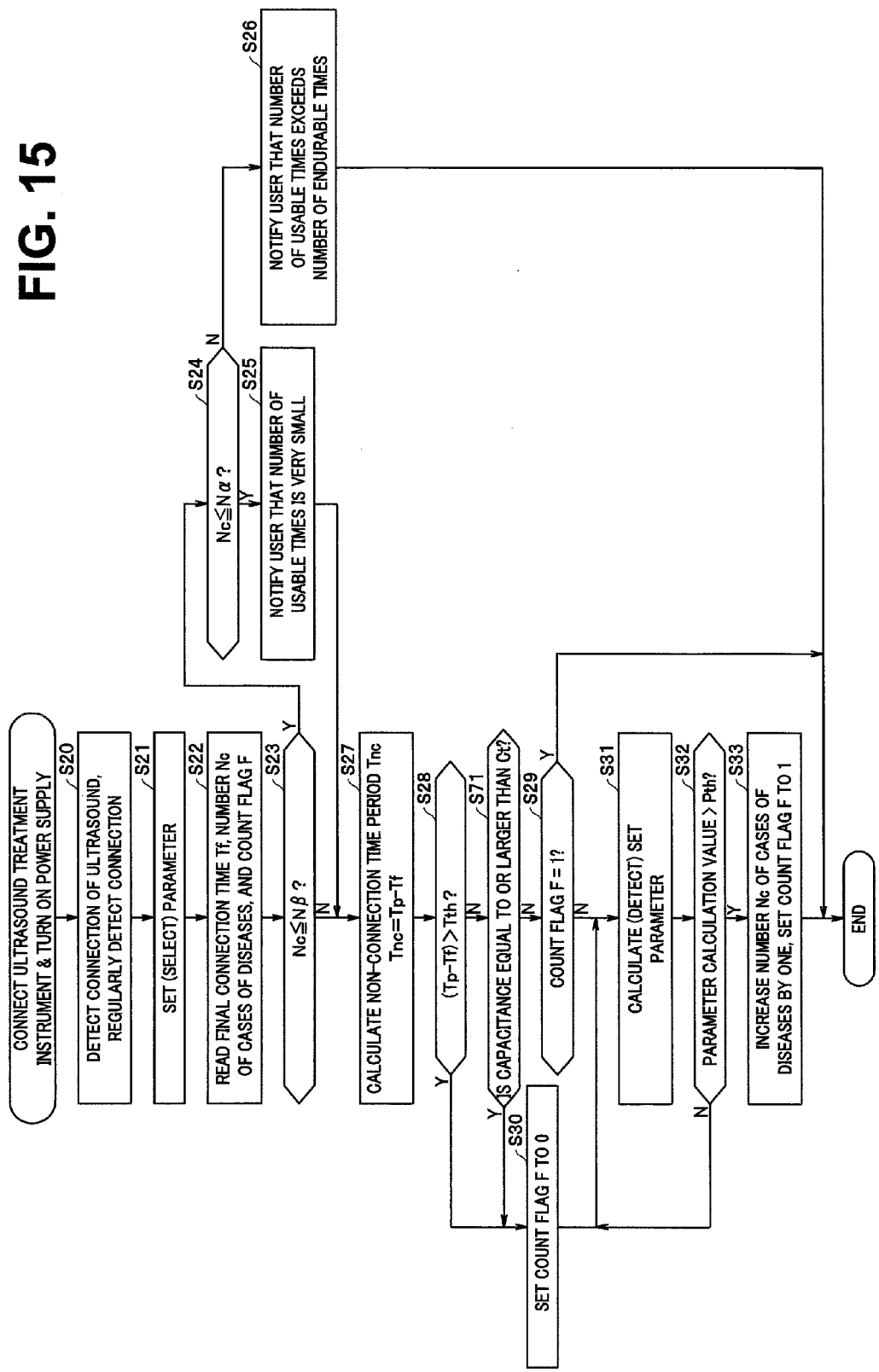
FIG. 15 is a flowchart showing a processing content using information of a capacitance.

Further, as shown in FIG. 2, a capacitance calculation section 51 that calculates (detects) a capacitance Cm which the ultrasound transducer 11 of the ultrasound treatment instrument 2 has is provided, and processing as shown in FIG. 15 may be performed with use of the calculated capacitance Cm.

As described as follows, in the processing shown in FIG. 15, even when the calculated non-connection time period (Tp−Tf) is shorter than the non-connection time period threshold value Tth, if the capacitance Cm calculated by the capacitance calculation section 51 is equal to or larger than a capacitance threshold value Ct that is set to a value larger than a capacitance that is calculated at a normal temperature, the flow proceeds to processing of step S30. When the calculated capacitance Cm is smaller than the capacitance threshold value Ct, the flow proceeds to processing of step S29. Note that the case of the former determination result is dealt similarly to the case of the determination result of (Tp−Tf)>Tth in FIG. 6.

In the processing shown in FIG. 15, processing of determining whether or not the capacitance C of the ultrasound transducer 11 is equal to or larger than the capacitance threshold value Ct shown in step S71 is performed between step S28 and step S29 in FIG. 6.

In step S71, the capacitance calculation section calculates the capacitance Cm of the ultrasound transducer 11 of the ultrasound treatment instrument 2, and outputs the capacitance Cm to the comparison section 26b. The comparison section 26b performs processing of determining whether or not the capacitance C is equal to or larger than the capacitance threshold value Ct.

When the capacitance C is equal to or larger than the capacitance threshold value Ct, the flow proceeds to processing of step S30, and when the capacitance C is less than the capacitance threshold value Ct conversely, the flow proceeds to the processing of step S29. The other processing is the processing similar to the case in FIG. 6.

The reason for performing the processing in FIG. 15 is as follows. Sterilization treatment of the ultrasound treatment instrument 2 is usually performed by the autoclave apparatus 5. In contrast with this, there is a flash method that performs sterilization treatment in a short time period under a sterilization treatment condition higher than a sterilization treatment condition that is usually adopted by the autoclave apparatus 5. In this case, the sterilization treatment can be performed in a shorter time period than under the ordinary sterilization treatment condition, and therefore, if a standard of a time required under the ordinary sterilization treatment condition is set to the non-connection time period threshold value, there can be the case in which the case of performing sterilization treatment by the flash method cannot be determined properly.

More specifically, when the ultrasound treatment instrument 2 is connected to the power supply apparatus 3 to be used in the next case of a disease after being subjected to sterilization treatment by the flash method, if determination of the non-connection time period is performed based on the ordinary non-connection time period threshold value which is set in response to the case of the ordinary sterilization treatment condition, the case occurs in which the non-connection time period is determined as a time period in which sterilization treatment is not performed.

When the ultrasound transducer 11 is in a higher temperature state than an ordinary temperature after being subjected to sterilization treatment by the flash method, the capacitance thereof has a capacitance larger than in the case of an ordinary temperature state. Therefore, as shown in FIG. 15, the capacitance of the ultrasound transducer 11 is determined by using the capacitance threshold value Ct larger than the capacitance which the ultrasound transducer 11 has in the ordinary temperature state, whereby it can be properly determined whether or not the ultrasound transducer 11 is the ultrasound transducer subjected to sterilization treatment by the flash method.

In this manner, the present processing properly determines whether or not the ultrasound treatment instrument 2 loaded with the ultrasound transducer 11 which is subjected to the sterilization treatment by the flash method is connected.

Note that in the processing shown in FIG. 15, the one non-connection time period threshold value Tth and the one capacitance threshold value Ct are used, but determination may be performed with use of a plurality of capacitance threshold values in accordance with the calculated non-connection time period (Tp−Tf).

Figures 16, 17:
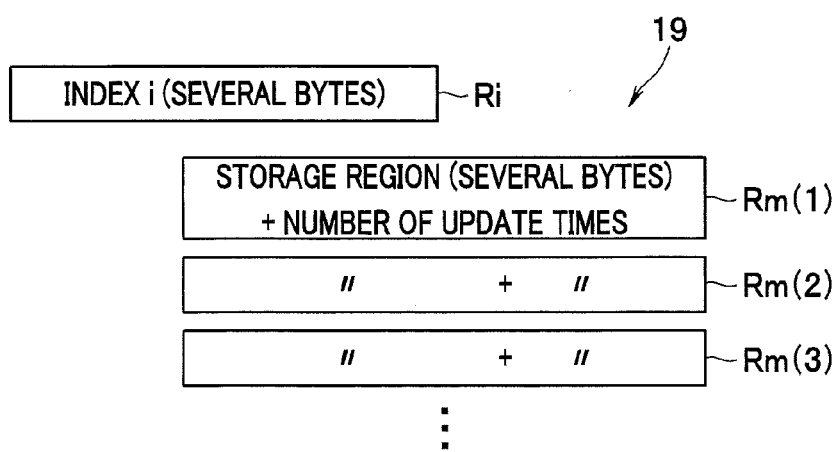
FIG. 16 is a diagram showing a setting example of non-connection time periods calculated when the processing in FIG. 15 is performed, and capacitance values corresponding thereto.
FIG. 17 is an explanatory diagram of an operation of performing storage by changing a storage region in accordance with an index when a present time is updated and stored in a storage section of the ultrasound treatment instrument.

FIG. 16 shows an example of a case of performing determination by using a plurality of capacitance threshold values in accordance with the calculated non-connection time period (Tp−Tf). In FIG. 16, when the non-connection time period (Tp−Tf) is 10 minutes to 20 minutes, for example, the capacitance threshold value is set to a capacitance Cn+240 pF at an ordinary temperature, and a case in which the capacitance of the ultrasound transducer 11 calculated by the capacitance calculation section is equal to or larger than Cn+240 pF is dealt similarly to the case in which the non-connection time period is determined as the non-connection time period exceeding the non-connection time period threshold value which is set in the case of the ordinary sterilization treatment condition of the autoclave apparatus. The cases of other non-connection time periods in FIG. 16 are similarly processed. Processing is performed as above, whereby even when a flash method is used, the number Nc of cases of diseases also can be counted precisely.

Further, when a storage device such as a flash memory is used as the aforementioned storage section 19, when the present time is regularly updated as the updated time in order to store (retain) the final connection time Tf, for example, a configuration may be adopted, in which a plurality of storage regions Rm(i) capable of being designated (specified) respectively by an index i (i=1, 2, . . . , n) are provided as shown in FIG. 17.

The maximum number of rewritable times of the storage device such as a flash memory that configures the storage section 19 is finite, and therefore, when the updated time (the present time) is regularly updated, the storage region Rm(i) is desirably changed at the times the number of which is smaller than the maximum number of times. Therefore, as shown in FIG. 17, the plurality of storage regions Rm(i) are provided in a storage region of the storage section 19, and an index region Ri in which the index i for designating the storage region Rm(i) which is used for storing the updated time (the present time) is retained (stored) is also secured in the storage region in the storage section 19.

For example, at first, the index i for the index region Ri is set to one, the updated time is regularly updated with use of the storage region Rm (1) which is designated by the index i(=1), and the number of updating times (the number of rewriting times) which is updated is also written at the same time. When the number of updating times reaches a predetermined number of times which is smaller than the maximum number of times, the index i is incremented by one and is set as i=2, and the updated time is regularly updated with use of a storage region Rm (2) which is designated by the index i(=2). The storage method like this is used, whereby the updated time can be reliably updated for a long period of time.

Note that in the embodiment including the aforementioned modification, a configuration in which a part of the configuration in FIG. 2 or the like is deleted may be adopted. Further, the configuration shown in FIG. 2 shows one configuration example, and is not limited to the case of the configuration example shown in FIG. 2. Further, in FIG. 7H and the like, the case of 60 minutes is described as the non-connection time period threshold value Tth as the non-connection time period Tnc of a predetermined time period, but FIG. 7H and the like are not limited to the case of this value, and the threshold values in the aforementioned parameters are not limited to the case of the specific values shown in the description.

As the parameter which is used to count the number Nc of cases of diseases as the number of times of use of the ultrasound treatment instrument 2, a parameter that is outputted (or supplied) to the ultrasound transducer 11 of the ultrasound treatment instrument 2 from the energy supply section may be used, or a parameter such as an output time period that is closely related to the parameter which is outputted (or supplied) may be set to be used.

Note that the explanation is given that the number Nc of cases of diseases can be precisely counted by the processing as shown in FIG. 6, for example, being performed with use of the count flag F, but the case of performing simpler processing also belongs to the present invention. For example, in FIG. 6, the processing of step S29 may be omitted.

More specifically, in the case of the determination result of (Tp−Tf)>Tth in step S28 in FIG. 6, the flow proceeds to step S30, and processing similar to the processing in FIG. 6 is performed, and in the case of the determination result of (Tp−Tf)≤Tth in step S28, the flow may be ended without performing the processing of step S29.

If the processing like this is performed, it can be distinguished, from the value of the count flag F at the next time of connection, whether the number Nc of cases of diseases is updated (as a result of the calculated value of the parameter exceeding the threshold value) and the flow is ended, or the number Nc of cases of diseases is not updated and the flow is ended, as the final result of the processing of step S31 and S32 with use of the set parameter.

Note that in the configuration shown in FIG. 2 described above or the like, the surgical system may be configured by the configuration including only the components corresponding to independent claim 1, or may be made a configuration to which one or a plurality of components added in accordance with necessity.

Further, the aforementioned embodiment and the like may be partially combined to form a different embodiment, or a modification may be configured.

What is claimed is:

1. A surgical system, comprising:
an ultrasound treatment instrument having an ultrasound transducer;
a power supply apparatus to which the ultrasound treatment instrument is detachably connected;
an energy supply section that is provided in the power supply apparatus, and supplies drive energy that causes the ultrasound transducer to be ultrasound-driven as output energy;
a clock that is provided in the power supply apparatus, and measures a present time;
a time updating section that is provided in the power supply apparatus, and outputs the present time;
a storage section that is provided in the ultrasound treatment instrument, stores a final updated time as an updated time that is at least finally updated in the present time which is outputted from the time updating section, and stores a number of times of use of the ultrasound treatment instrument;
a time period calculation section that calculates a non-connection time period in which the ultrasound treatment instrument and the power supply apparatus are not connected based on a difference between the final updated time which is stored in the storage section, and the present time by the clock;
a comparison section that determines whether or not the non-connection time period which is calculated in the time period calculation section exceeds a predetermined time period;
a processing section that performs processing of generating an update signal that causes the number of times of use to be updated in accordance with a result of determination with respect to a parameter including at least one of a number of output times of the drive energy, an output time period of the drive energy, an output power of the drive energy, an output current integrated value of the drive energy, an output voltage integrated value of the drive energy, an output power integrated value of the drive energy, a continuous output time period of the drive energy, an output time period integrated value of the drive energy, and a connection time period of the ultrasound treatment instrument and the power supply apparatus, when it is determined in the comparison section that the non-connection time period exceeds the predetermined time period; and
a number of times of use updating section that updates the number of times of use based on the update signal.

2. The surgical system according to claim 1, wherein the processing section performs processing of not generating the update signal which updates the number of times of use when it is determined that the non-connection time period does not exceed the predetermined time period.

3. The surgical system according to claim 1, wherein the storage section is provided in the ultrasound treatment instrument, stores the final updated time as the updated time which is at least finally updated in the present time which is regularly outputted from the time updating section, and stores the number of times of use of the ultrasound treatment instrument, and number of times update identification information as identification information on whether or not a flag state is a flag state in which the number of times of use in a case of the ultrasound treatment instrument being connected to the power supply apparatus at a previous time is updated,
the processing section performs first processing of whether or not to generate the update signal which updates the number of times of use in accordance with a case of an identification result of the number of times update identification information by further identifying the number of times update identification information, in a case of a determination result that the non-connection time period does not exceed the predetermined time period, and
performs second processing of generating the update signal in accordance with a determination result with respect to the parameter, after setting the flag state to a flag state in which the number of times update identification information is not updated, in a case of a determination result that the non-connection time period exceeds the predetermined time period.

4. The surgical system according to claim 3, wherein when the processing section performs the first processing, the processing section does not update the number of times of use in a case of an identification result of the flag state in which the number of times update identification information is updated, and
performs processing of generating the update signal which updates the number of times of use in accordance with the determination result with respect to the parameter in a case of an identification result that the flag state is not the flag state in which the number of times update identification information is updated.

5. The surgical system according to claim 3, wherein when the processing section performs the second processing, the processing section performs processing of generating the update signal which causes the number of times of use to be updated, and updating the number of times of use update identification information, in a case of a determination result of exceeding a parameter threshold value that is set to the parameter in advance, with respect to a calculation value of the parameter.

6. The surgical system according to claim 1, further comprising:
a number of output times calculation section that calculates the number of output times at which the drive energy is outputted to the ultrasound transducer from the energy supply section, in a state in which the ultrasound treatment instrument is connected to the power supply apparatus,
wherein when the number of output times as the parameter exceeds a number of output times threshold value that is set in advance, the processing section generates the update signal that causes the number of times of use to be updated, and
the number of times of use updating section updates the number of times of use to increase the number of times of use by one.

7. The surgical system according to claim 1, wherein the parameter is an output parameter in a case in which the drive energy is outputted to the ultrasound transducer from the energy supply section, and
the processing section performs processing of generating the update signal which causes the number of times of use to be updated based on a determination result with respect to the output parameter which is outputted to the ultrasound transducer.

8. The surgical system according to claim 7, further comprising:
an output time period calculation section that calculates the output time period in which the drive energy is actually outputted to the ultrasound transducer from the energy supply section, in a state in which the ultrasound treatment instrument is connected to the power supply apparatus,
wherein the processing section generates the update signal which causes the number of times of use to be updated when the output time period of the drive energy as the output parameter exceeds an output time period threshold value that is set in advance, and
the number of times of use updating section updates the number of times of use to increase the number of times of use by one.

9. The surgical system according to claim 8, wherein the output time period calculation section calculates the continuous output time period in which continuous output is performed as the output time period,
the processing section generates the update signal which causes the number of times of use to be updated when the continuous output time period in which the drive energy is continuously outputted to the ultrasound transducer from the energy supply section exceeds a continuous output time period threshold value that is set in advance, and
the number of times of use updating section updates the number of times of use to increase the number of times of use by one.

10. The surgical system according to claim 8, wherein the output time period calculation section calculates the output time period integrated value that is the output time period integrated in the state in which the ultrasound treatment instrument is connected to the power supply apparatus,
the processing section generates the update signal which causes the number of times of use to be updated when the output time period integrated value exceeds an output time period integration threshold value that is set in advance, and
the number of times of use updating section updates the number of times of use to increase the number of times of use by one.

11. The surgical system according to claim 5, wherein the parameter is an output parameter relating to the drive energy which is outputted to the ultrasound transducer from the energy supply section.

12. The surgical system according to claim 11, further comprising:
a current integrated value calculation section that calculates at least any one of an integrated value of an output current, an integrated value of an output voltage, and an integrated value of output power, which configure the drive energy which is outputted to the ultrasound transducer from the energy supply section, in a state in which the ultrasound treatment instrument is connected to the power supply apparatus,
wherein the processing section generates the update signal which causes the number of times of use to be updated when at least any one of a threshold value of the integrated value of the output current, a threshold value of the integrated value of the output voltage, and a threshold value of the integrated value of the output power which are set in advance as the output parameters is exceeded, and
the number of times of use updating section updates the number of times of use to increase the number of times of use by one.

13. The surgical system according to claim 1, further comprising:
a second storage section that stores in advance a first number of times of use threshold value as a maximum number of times of use corresponding to a lifespan of the ultrasound treatment instrument, and a second number of times of use threshold value that is smaller than the first number of times of use threshold value by at least one time;
a second comparison section that compares the number of times of use which is read from the storage section, with the first number of times of use threshold value and the second number of times of use threshold value which are read from the second storage section; and
a notification section that notifies a user that the number of times of use exceeds the first number of times of use threshold value or the second number of times of use threshold value, when the number of times of use exceeds the first number of times of use threshold value or the second number of times of use threshold value, based on a comparison result by the second comparison section.

14. The surgical system according to claim 1, wherein the time updating section outputs the present time which is measured by the clock to the storage section at each set time as the updated time to be updated, and the storage section stores the present time to be updated which is outputted from the time updating section as the updated time which updates an old present time that is stored before the set time, in a case of a state in which the ultrasound treatment instrument is connected to the power supply apparatus.

15. The surgical system according to claim 1, wherein
the storage section has a plurality of storage regions for storing the updated time, and
when the storage section stores the updated time, the storage section stores index information that specifies the storage region for storing the updated time, and information of a number of times of update at which the updated time is updated, and when the number of times of update reaches a predetermined number of times, the storage section changes the index information, and stores the updated time by using another storage region that is specified by the changed index information and is different from the storage region.

16. The surgical system according to claim 1, wherein
the storage section further stores a shipping date and time at which the ultrasound treatment instrument is shipped as a product,
the surgical system further comprising:
an elapsed days and time period calculation section that calculates elapsed days and time period from the shipping date and time to a connection date and time from a difference in date and time between the connection date and time when the ultrasound treatment instrument is connected to the power supply apparatus, and the shipping date and time which is read from the storage section at the connection date and time;
a second comparison section that compares whether or not the elapsed days and time period calculated by the elapsed days and time period calculation section exceeds a first elapsed days and time period threshold value that is set in advance with respect to the ultrasound treatment instrument, and a second elapsed days and time period threshold value that is smaller by at least one day than the first elapsed days and time period threshold value; and
a notification section that notifies a user that the elapsed days and time period exceeds the first elapsed days and time period threshold value or the second elapsed days and time period threshold value, when the elapsed days and time period exceeds the first elapsed days and time period threshold value or the second elapsed days and time period threshold value, based on a comparison result by the second comparison section.

17. The surgical system according to claim 1, further comprising:
a capacitance calculation section that calculates a capacitance of the ultrasound transducer, and determines whether or not the calculated capacitance exceeds a capacitance threshold value that is set in advance,
wherein the processing section performs processing of generating the update signal which causes the number of times of use to be updated based on a determination result with respect to the parameter, when it is determined that the capacitance exceeds the capacitance threshold value.

* * * * *